(12) United States Patent
Nomura et al.

(10) Patent No.: US 10,760,799 B2
(45) Date of Patent: Sep. 1, 2020

(54) ULTRAVIOLET STERILIZER AND AIR CONDITIONING APPARATUS USING THE SAME

(71) Applicant: Mitsubishi Electric Corporation, Chiyoda-ku (JP)

(72) Inventors: Akane Nomura, Chiyoda-ku (JP); Akira Morikawa, Chiyoda-ku (JP); Isamu Hirashiki, Chiyoda-ku (JP); Junichiro Horiuchi, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 15/775,077

(22) PCT Filed: Jul. 8, 2016

(86) PCT No.: PCT/JP2016/070346
§ 371 (c)(1),
(2) Date: May 10, 2018

(87) PCT Pub. No.: WO2017/119152
PCT Pub. Date: Jul. 13, 2017

(65) Prior Publication Data
US 2018/0356109 A1    Dec. 13, 2018

(30) Foreign Application Priority Data
Jan. 7, 2016    (JP) .................. 2016-001972

(51) Int. Cl.
*F24F 3/16* (2006.01)
*A61L 9/20* (2006.01)
(Continued)

(52) U.S. Cl.
CPC .............. *F24F 3/166* (2013.01); *A61L 9/20* (2013.01); *F24F 1/00* (2013.01); *F24F 1/02* (2013.01);
(Continued)

(58) Field of Classification Search
None
See application file for complete search history.

(56) References Cited

U.S. PATENT DOCUMENTS 9,168,321 B2 * 10/2015 Oestergaard .............. A61L 2/10
9,233,857 B2 * 1/2016 Nikamoto .............. C02F 1/325
(Continued)

FOREIGN PATENT DOCUMENTS

EP    1 365 197    11/2003
EP    2 921 183 A1    9/2015
(Continued)

OTHER PUBLICATIONS

Office Action dated Feb. 6, 2017 in Japanese application No. 2016-564642 (with partial English translation).
(Continued)

*Primary Examiner* — Andrew Smyth
(74) *Attorney, Agent, or Firm* — Xsensus LLP

(57) ABSTRACT

An air-conditioning apparatus that conditions introduced air includes an ultraviolet sterilizer that emits ultraviolet ray to the air. The ultraviolet sterilizer includes a sterilizing light screen forming unit that forms a screen-shaped sterilizing light screen based on the emitted ultraviolet ray.

18 Claims, 15 Drawing Sheets

(51) Int. Cl.
- *F24F 1/00* (2019.01)
- *H01L 33/60* (2010.01)
- *G02B 5/08* (2006.01)
- *F24F 1/02* (2019.01)

(52) U.S. Cl.
CPC ............ *G02B 5/08* (2013.01); *G02B 5/0891* (2013.01); *H01L 33/60* (2013.01); *A61L 2209/12* (2013.01); *A61L 2209/14* (2013.01); *A61L 2209/16* (2013.01); *F24F 2003/1667* (2013.01)

(56) References Cited

U.S. PATENT DOCUMENTS

| | | | | |
|---|---|---|---|---|
| 2004/0022050 | A1* | 2/2004 | Yamashita | G02B 6/0021 362/615 |
| 2009/0289205 | A1* | 11/2009 | Moriya | G03F 7/70575 250/504 R |
| 2010/0027294 | A1* | 2/2010 | Lee | G02B 5/02 362/620 |
| 2010/0039707 | A1* | 2/2010 | Akahane | G02B 3/0012 359/576 |
| 2010/0182308 | A1* | 7/2010 | Holman | G02B 6/0028 345/214 |
| 2012/0168641 | A1* | 7/2012 | Lizotte | A61L 9/20 250/435 |
| 2013/0114062 | A1* | 5/2013 | Liesener | H01L 21/681 355/72 |
| 2014/0252249 | A1* | 9/2014 | Doros | F21V 5/043 250/504 R |
| 2015/0129777 | A1 | 5/2015 | Nikamoto | |
| 2015/0250913 | A1* | 9/2015 | Matsui | A61L 2/10 250/436 |
| 2017/0217791 | A1* | 8/2017 | McNulty | C02F 1/325 |

FOREIGN PATENT DOCUMENTS

| | | |
|---|---|---|
| JP | 2002-172157 | 6/2002 |
| JP | 2003-144537 A | 5/2003 |
| JP | 2003-207166 A | 7/2003 |
| JP | 2005-304979 A | 11/2005 |
| JP | 2013-240487 A | 12/2013 |
| JP | 2014-100206 A | 6/2014 |
| WO | WO 2013/064154 A1 | 5/2013 |
| WO | WO 2014/058011 A1 | 4/2014 |

OTHER PUBLICATIONS

International Search Report dated Aug. 9, 2016 in PCT/JP2016/070346, filed on Jul. 8, 2016.
Extended Search Report dated Nov. 19, 2018 in European Patent Application No. 16883653.4, 9 pages.
Combined Office Action and Search Report dated Dec. 17, 2018 in Chinese Patent Application No. 201680072952.1, 14 pages (with English translation and English translation of categories of cited documents).
European Office Action issued in European Patent Application No. 16883653.4 dated Jun. 27, 2019.
Chinese Office Action issued in Chinese Patent Application No. 201680072952.1 dated Apr. 11, 2019 (w/ English translation).
Chinese Office Action issued in Chinese Patent Application No. 201680072952.1 dated Aug. 2, 2019 (w/ English Translation).

* cited by examiner

FIG. 11

| | EMITTING PORTION | REFLECTOR 3A | REFLECTOR 3E | REFLECTOR 3J | REFLECTOR 3C | REFLECTOR 3H | REFLECTOR 3D | REFLECTOR 3I | REFLECTOR 3B | REFLECTOR 3G | REFLECTOR 3K | REFLECTOR 3F |
|---|---|---|---|---|---|---|---|---|---|---|---|---|
| ULTRAVIOLET LIGHT IRRADIANCE (mW·S/cm²) | 2.62 | 5.19 | 5.07 | 4.94 | 4.85 | 4.77 | 4.70 | 4.65 | 4.60 | 4.57 | 4.55 | 2.28 |

FIG. 12

SURVIVAL RATE OF AIRBORNE INFLUENZA (y-axis, 0.00001 to 1)
ULTRAVIOLET LIGHT IRRADIANCE (mW·S/cm²) (x-axis, 0 to 5)

FIG. 13

| WAVE-LENGTH | ENERGY E(eV) | STERILIZING EFFECT | STERILIZING EFFECT PER 1 eV AT EACH WAVELENGTH |
|---|---|---|---|
| 200 | 6.20 | 0.15 | 0.024 |
| 220 | 5.64 | 0.25 | 0.044 |
| 240 | 5.17 | 0.63 | 0.122 |
| 250 | 4.96 | 0.91 | 0.183 |
| 260 | 4.77 | 0.99 | 0.208 |
| 280 | 4.43 | 0.60 | 0.135 |
| 290 | 4.28 | 0.30 | 0.070 |
| 300 | 4.13 | 0.06 | 0.0145 |
| 320 | 3.88 | 0.004 | 0.00103 |
| 340 | 3.65 | 0.0009 | 0.00025 |
| 360 | 3.44 | 0.0003 | 0.00009 |

| | EMITTING PORTION (3Dd) | RE-FLEC-TOR 3Ad | RE-FLEC-TOR 3Cd | RE-FLEC-TOR 3Ed | RE-FLEC-TOR 3Bd |
|---|---|---|---|---|---|
| ULTRAVIOLET LIGHT IRRADIANCE (mW·S/cm²) | 2.66 | 2.86 | 2.72 | 2.58 | 2.45 |

US 10,760,799 B2

ULTRAVIOLET STERILIZER AND AIR CONDITIONING APPARATUS USING THE SAME

TECHNICAL FIELD

The present invention relates to an ultraviolet sterilizer intended for airborne microbes, such as bacteria, fungi and viruses, in the air as treating objects and an air-conditioning apparatus on which the ultraviolet sterilizer is mounted.

BACKGROUND ART

It is known that ultraviolet ray having a wavelength of 200 nm to 360 nm not only takes a proliferating ability by acting on nucleic acid that is the protoplasm of bacteria to inhibit replication of DNA but also kills bacteria by destroying proteins, and other substances, that are formative substances of cytoplasm and cell membranes. An ultraviolet sterilizer that sterilizes air, or the like, by emit such ultraviolet ray is in actual use. The ultraviolet sterilizer is to sterilize microbes in the air by emit ultraviolet ray to influent air, and the like (see, for example, Patent Literature 1 and Patent Literature 2).

In the ultraviolet sterilizer of Patent Literature 1, in order for emit ultraviolet ray not to leak from a sterilizing chamber inside a casing that is a box, an upper portion of one of two facing sides in a sterilizing chamber is open as an air intake, a lower portion of the other one of the sides is open as an outlet opening, and air is caused to pass through the inside of the sterilizing chamber via these opening ports.

In the ultraviolet sterilizer of Patent Literature 2, to increase the irradiance of ultraviolet ray inside the sterilizer, reflectors are installed on wall surfaces inside a flow passage through which fluid flows, and ultraviolet ray is reflected multiple times by emitting ultraviolet ray obliquely to the reflectors. Thus, the ultraviolet sterilizer sterilizes fluid.

CITATION LIST

Patent Literature

Patent Literature 1: Japanese Unexamined Patent Application Publication No. 2014-100206
Patent Literature 2: Japanese Unexamined Patent Application Publication No. 2013-240487

SUMMARY OF INVENTION

Technical Problem

However, the ultraviolet sterilizer of Patent Literature 1 requires a large number of ultraviolet ray emitting diodes and a relatively wide sterilizing chamber. The ultraviolet sterilizer of Patent Literature 2 has a wide ultraviolet ray irradiation range in a fluid traveling direction to increase the irradiance of ultraviolet ray by causing ultraviolet ray to be reflected multiple times. That is, the existing ultraviolet sterilizers have poor sterilizing efficiency per unit volume and need to be increased in size.

The present invention has been made to solve the above-described problems, and it is an object of the present invention to provide an ultraviolet sterilizer and an air-conditioning apparatus that efficiently sterilize fluid with a compact space.

Solution to Problem

An ultraviolet sterilizer of one embodiment of the present invention sterilizes air by using ultraviolet ray, and includes an ultraviolet sterilizer configured to emit ultraviolet ray to the air, the ultraviolet sterilizer including a sterilizing light screen forming unit configured to form a screen-shaped sterilizing light screen based on the emitted ultraviolet ray.

An air-conditioning apparatus of one embodiment of the present invention conditions introduced air. The air-conditioning apparatus includes an ultraviolet sterilizer that emits ultraviolet ray to the air. The ultraviolet sterilizer includes a sterilizing light screen forming unit that forms a screen-shaped sterilizing light screen based on the emitted ultraviolet ray.

Advantageous Effects of Invention

With the embodiments of the present invention, the sterilizing light screen forming unit forms a screen-shaped sterilizing light screen by emitting ultraviolet ray, so it is possible to efficiently sterilize fluid with a compact space.

BRIEF DESCRIPTION OF DRAWINGS

FIG. 11 is a table that shows an ultraviolet ray irradiance at the level of 1 mm above each reflector shown in FIG. 3.

FIG. 12 is a graph that shows the relation between an ultraviolet ray irradiance provided by the ultraviolet sterilizer shown in FIG. 3 and a survival rate of airborne influenza virus.

FIG. 13 is a table that shows an energy (eV), a sterilizing effect and a sterilizing effect per 1 eV by wavelength where a plurality of wavelengths of ultraviolet ray is set in the range of 200 nm to 360 nm.

DESCRIPTION OF EMBODIMENTS

Embodiment 1

Figure 1:
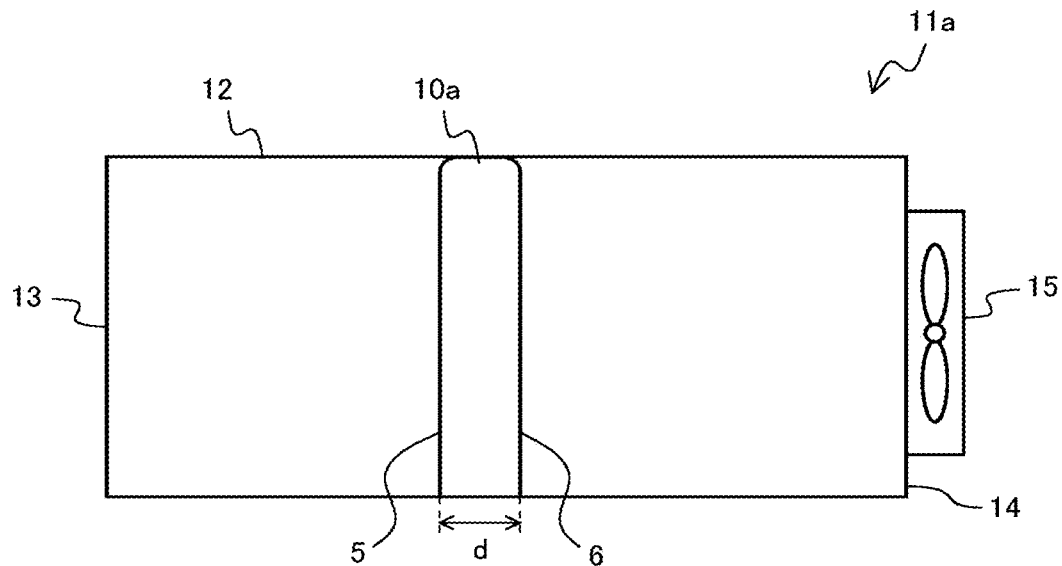
FIG. 1 is a schematic diagram that shows the schematic configuration of an air-conditioning apparatus according to Embodiment 1 of the present invention.
Figure 2:
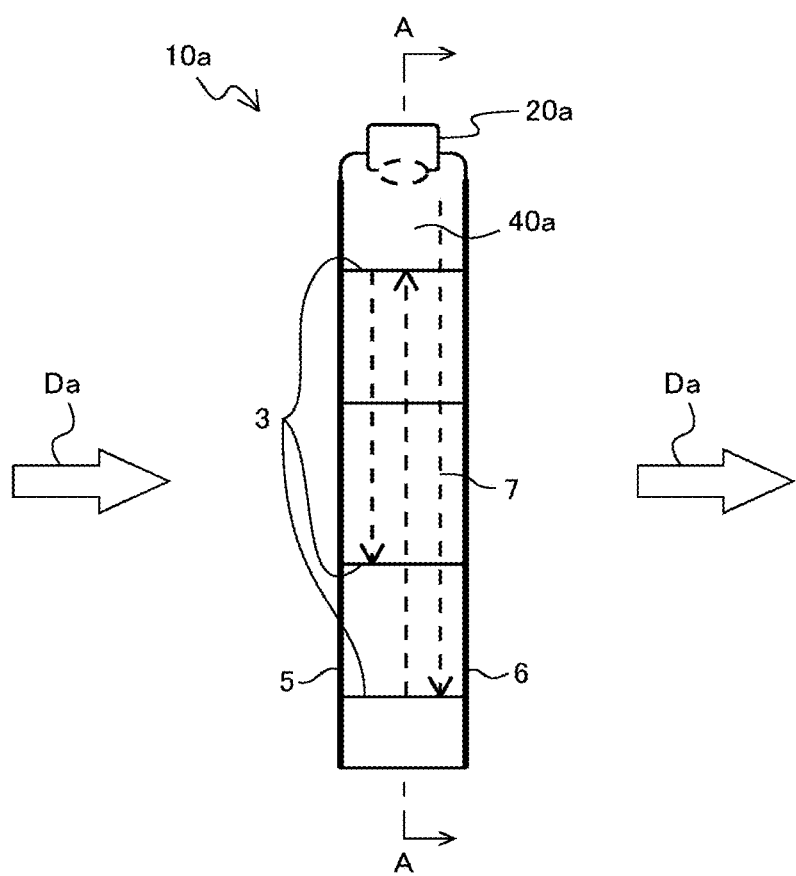
FIG. 2 is a diagram that shows the schematic configuration of an ultraviolet sterilizer of the air-conditioning apparatus shown in FIG. 1.
Figure 3:
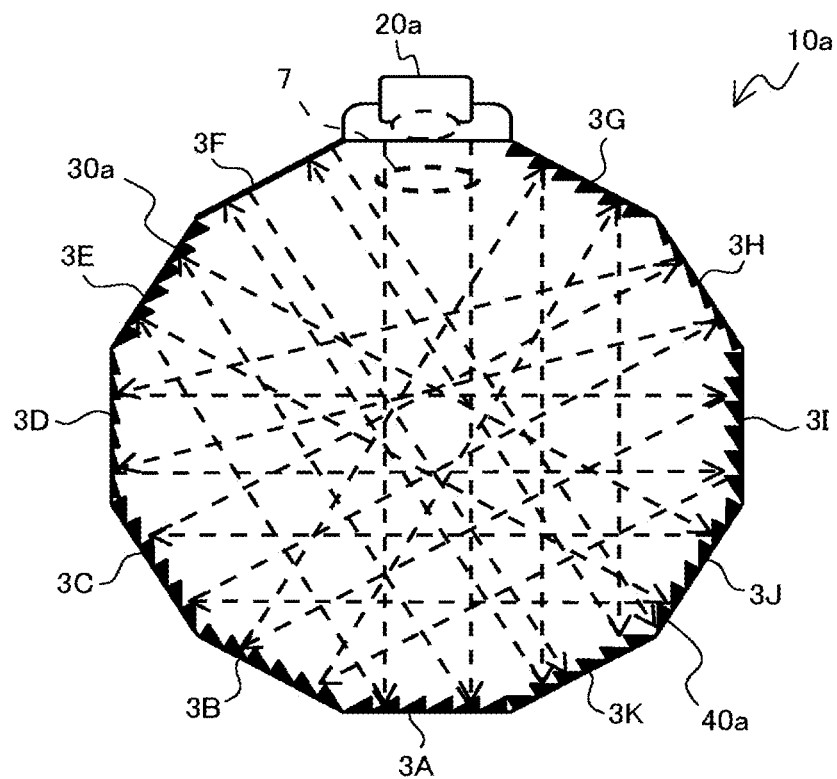
FIG. 3 is a schematic cross-sectional view of the ultraviolet sterilizer, taken along the line A-A in FIG. 2.
Figure 4:
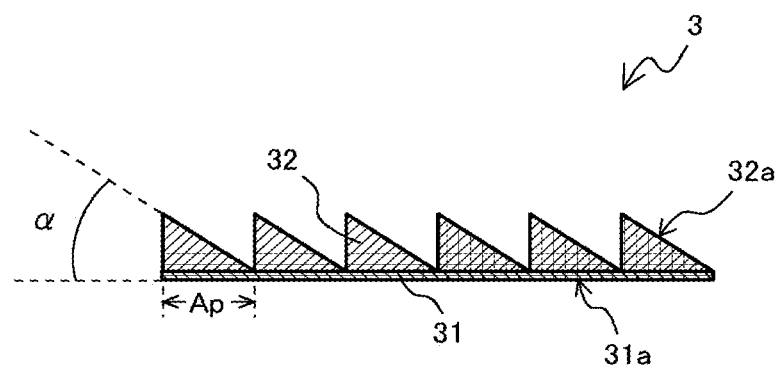
FIG. 4 is a diagram that illustrates the shape of each reflector of the ultraviolet sterilizer shown in FIG. 3.

FIG. 1 is a schematic diagram that shows the schematic configuration of an air-conditioning apparatus according to Embodiment 1. FIG. 2 is a diagram that shows the schematic configuration of an ultraviolet sterilizer of the air-conditioning apparatus shown in FIG. 1. FIG. 3 is a schematic cross-sectional view of the ultraviolet sterilizer, taken along the line A-A in FIG. 2. FIG. 4 is a diagram that illustrates the shape of each reflector of the ultraviolet sterilizer shown in FIG. 3. The configuration of the ultraviolet sterilizer according to Embodiment 1 and the configuration of the air-conditioning apparatus using the ultraviolet sterilizer will be described with reference to FIG. 1 to FIG. 4.

As shown in FIG. 1, the air-conditioning apparatus 11a includes a cylindrical casing 12. The cylindrical casing 12 has an air intake 13 and an outlet opening 14. The air intake 13 introduces air. Through the outlet opening 14 the air introduced from the air intake 13 flows out. The air-conditioning apparatus 11a includes the ultraviolet sterilizer 10a and an air-sending device 15. The ultraviolet sterilizer 10a is disposed between the air intake 13 and the outlet opening 14. The ultraviolet sterilizer 10a sterilizes air. The air-sending device 15 generates flow of air from the air intake 13 toward the outlet opening 14. A direction from the air intake 13 toward the outlet opening 14 is defined as a flow direction.

The casing 12 has a circular shape in cross section taken along a plane perpendicular to the flow direction. In Embodiment 1, the diameter of the circular shape in the cross section of the casing 12 is 100 mm. The air-sending device 15 has the function of sending air at a velocity of 3 m/s.

As shown in FIG. 2, the ultraviolet sterilizer 10a includes a sterilizing light screen forming unit. The sterilizing light screen forming unit forms a screen-shaped sterilizing light screen based on emitted ultraviolet ray. Specifically, the ultraviolet sterilizer has a cylindrical casing 40a. The cylindrical casing 40a has an inlet port 5 and an outlet port 6. Air flows into the inlet port 5. The air flowing from the inlet port 5 flows out through the outlet port 6. That is, the cylindrical casing 40a has a shape such that both sides are open through the inlet port 5 and the outlet port 6. As shown in FIG. 2 and FIG. 3, the ultraviolet sterilizer 10a includes an emitting portion 20a and a reflecting portion 30a. The emitting portion 20a is disposed at the outer peripheral portion of the cylindrical casing 40a, and serves as an ultraviolet ray source. The reflecting portion 30a is disposed on the inner surface of the cylindrical casing 40a, and reflects ultraviolet ray. A direction from the inlet port 5 toward the outlet port 6 is defined as an outflow direction. The ultraviolet sterilizer 10a is disposed inside the casing 12 such that the outflow direction agrees with the flow direction. That is, the outflow direction and the flow direction are the same direction as an air flow direction Da shown in FIG. 2. Hereinafter, the shape of a cross section taken along a plane perpendicular to the flow direction and the outflow direction is simply referred to as a cross-sectional shape. The cross-sectional shape corresponds to a front view when viewed from the inlet port 5 side in the axial longitudinal direction of the cylindrical casing 40a. In Embodiment 1, it is assumed that the thickness d of the ultraviolet sterilizer 10a along the air flow direction Da is 1 cm or 10 cm.

The broken line arrows 7 in FIG. 2 and FIG. 3 indicate fluxes of ultraviolet ray that are emitted from the emitting portion 20a and that are reflected on reflectors 3 and also indicate the traveling directions of the fluxes of ultraviolet ray. The broken line arrows 7 in FIG. 2 illustrate the optical axes of the fluxes of ultraviolet ray and the traveling directions of the fluxes of ultraviolet ray in a simplified manner. The broken line arrows 7 in FIG. 3 illustrate the fluxes of ultraviolet ray and the traveling directions of the fluxes of ultraviolet ray. The emitting portion 20a is to emit a flux of ultraviolet ray, that is, a flux of rays; however, hereinafter, a flux of ultraviolet ray that the emitting portion 20a emits is also simply referred to as ultraviolet ray.

The cross-sectional shape of the cylindrical casing 40a is a regular dodecagonal shape. The cross-sectional view is the front view when viewed from the inlet port 5 side in the axial longitudinal direction of the cylindrical casing 40a. The emitting portion 20a is disposed at the outer peripheral portion of the cylindrical casing 40a. More specifically, emitting portion 20a is disposed at a location corresponding to one of the sides of the regular dodecagonal shape that is the cross-sectional shape of the cylindrical casing 40a. The emitting portion 20a includes one or more ultraviolet ray emitting elements (not shown), and emits ultraviolet ray in a direction perpendicular to the outflow direction and toward the inner side of the cylindrical casing 40a. The emitting portion 20a in Embodiment 1 is a UV-LED light source in which a collimate lens that is able to emit parallel rays having a wavelength of 254 nm at 0.1 W/cm² to 5.0 W/cm² is installed. The UV-LED light source that serves as the emitting portion 20a desirably emits parallel rays having a wavelength of 254 nm at 0.4 W/cm².

The reflecting portion 30a is disposed on the inner surface of the cylindrical casing 40a of which the cross-sectional shape is a regular dodecagonal shape. The reflecting portion 30a is provided such that the cross-sectional shape is a regular dodecagonal annular shape. In the reflecting portion 30a, at least part of the shape of a surface that is a surface that reflects ultraviolet ray is a prism shape. The reflecting portion 30a reflects ultraviolet ray, emitted from the emitting portion 20a, multiple times on a plane perpendicular to the outflow direction, that is, along the radial direction of the cylindrical casing 40a. The plane perpendicular to the outflow direction, on which ultraviolet ray is reflected, has a thickness corresponding to a flux of ultraviolet ray that is emitted in form of parallel rays.

The reflecting portion 30a includes the plurality of reflectors 3A to 3J that reflect ultraviolet ray. The reflectors 3A to 3K respectively constitute the sides of the regular dodecagonal shape that is the cross-sectional shape of the reflecting portion 30a. That is, as shown in FIG. 3, the reflectors 3A to 3K are respectively disposed at the locations of the eleven sides of the regular dodecagonal shape that is the cross-sectional shape of the reflecting portion 30a, and a line segment that connects an emitting portion 20a-side end of the reflector 3F to an emitting portion 20a-side end of the reflector 3G is a remaining one side. Hereinafter, the reflectors 3A to 3K are also simply collectively referred to as the reflectors 3 or any one of the reflectors 3A to 3K is also simply referred to as the reflector 3.

As shown in FIG. 4, each reflector 3 includes a flat part 31 along the inner surface of the cylindrical casing 40a and a reflecting part 32 located on the inner surface side of the flat part 31. That is, each reflector 3 is provided such that the thin-plate flat part 31 and the reflecting part 32 having a prism-shaped surface are integrally formed.

In the flat part 31, a flat surface 31a that is a surface facing the inner surface of the cylindrical casing 40a is flat. The cross-sectional shape of the reflecting part 32 is a shape such that right-angled triangles each having a hypotenuse at an inclination angle of α relative to the flat surface 31a are arranged side by side, and a surface corresponding to each hypotenuse serves as a reflecting surface 32a that reflects ultraviolet ray. The inclination angle α of each of the reflectors 3A to 3J is set in advance such that ultraviolet ray travels widely over the entire area inside the cylindrical casing 40a. In Embodiment 1, the surface shape of the reflecting part 32 having a cross-sectional shape such that right-angled triangles are arranged side by side is referred to as prism shape.

The inclination angle α and inclination direction of the reflecting surface 32a relative to the flat surface 31a of each reflector 3 will be specifically described. On the inner surface of the cylindrical casing 40a, the reflector 3A is provided at a location facing the emitting portion 20a, and the reflectors 3B to 3K are provided clockwise from the location at which the reflector 3A is provided. The emitting portion 20a is disposed such that ultraviolet ray to be emitted is vertically emit to the reflector 3A. Since the cross-sectional shape of the ultraviolet sterilizer 10a is a regular dodecagonal shape, there are the facing reflectors 3 for the respective reflectors 3.

As shown in FIG. 3, each of the reflector 3A, the reflector 3G, the reflector 3I and the reflector 3J has a prism shape such that the inclination angle α is 15° and upward sloping. Each of the reflector 3B, the reflector 3C, the reflector 3E and the reflector 3K has a prism shape such that the inclination angle α is 15° and downward sloping. The reflector 3D has a prism shape such that the inclination angle α is 7.5° and upward sloping. The reflector 3H has a prism shape such that the inclination angle α is 7.5° and downward sloping. The reflector 3F has a flat surface.

Figure 5:
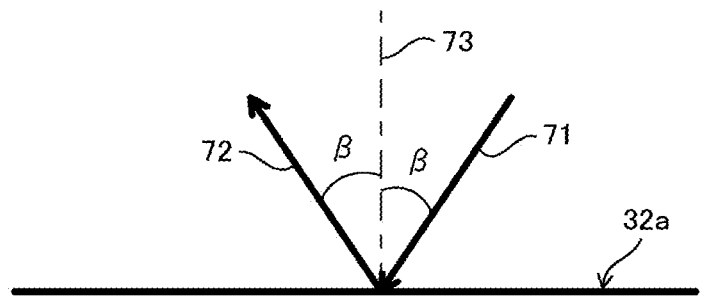
FIG. 5 is a diagram regarding an incident angle of light and a reflection angle of the light.
Figure 6:
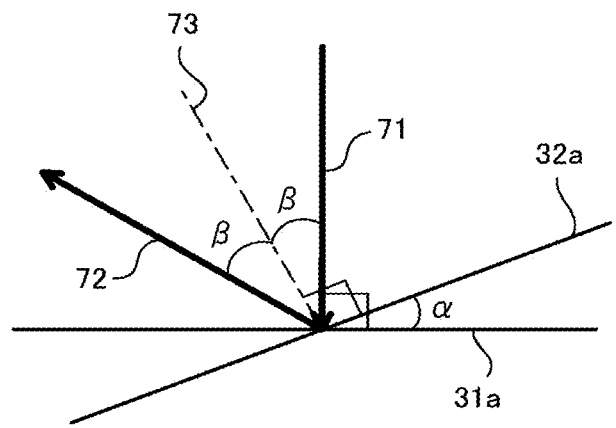
FIG. 6 is a schematic diagram that shows an inclination angle of a reflecting surface relative to a flat surface in the case where ultraviolet ray vertically enters the reflector illustrated in FIG. 4.
Figure 7:
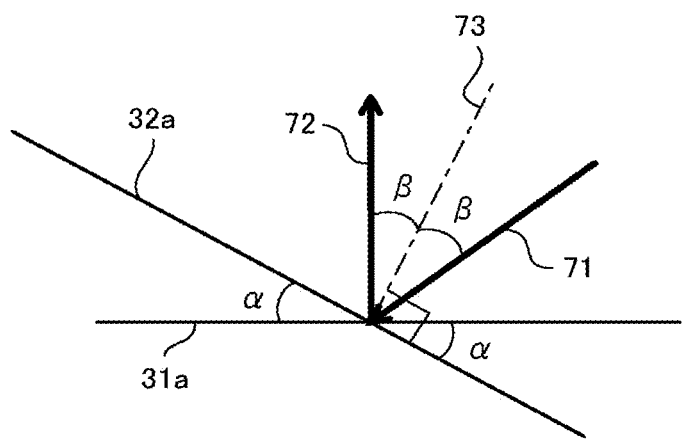
FIG. 7 is a schematic diagram that shows an inclination angle of a reflecting surface relative to a flat surface in the case where ultraviolet ray is vertically reflected from the reflector illustrated in FIG. 4.

FIG. 5 is a diagram regarding an incident angle of light and a reflection angle of the light. FIG. 6 is a schematic diagram that shows an inclination angle of the reflecting surface 32a relative to the flat surface 31a in the case where ultraviolet ray vertically enters the reflector 3. FIG. 7 is a schematic diagram that shows an inclination angle of the reflecting surface 32a relative to the flat surface 31a in the case where ultraviolet ray is vertically reflected from the reflector 3.

As shown in FIG. 5, when light passes through the air and is reflected by a metal plate, or the like, the law of reflection, that is, the incident angle of incident light 71 is equal to the reflection angle of reflected light 72, holds. In FIG. 5, the incident angle and the reflection angle are denoted by β. Each of the incident angle and the reflection angle is defined as an angle between the traveling direction of corresponding light and a normal 73 that is the perpendicular to the reflecting surface 32a.

As shown in FIG. 6, in the case where the inclination angle α is set, when ultraviolet ray vertically enters the flat surface 31a of the reflector 3, the inclination angle α is equal to the incident angle and the reflection angle. For this reason, by providing the reflecting surface 32a having the inclination angle α that is the same as the reflection angle commensurate with a direction in which ultraviolet ray is intended to be reflected and causing the ultraviolet ray to vertically enter the flat surface 31a, it is possible to control the traveling direction of the reflected light 72 relative to the incident light 71.

As shown in FIG. 7, when ultraviolet ray is intended to be reflected vertically relative to the flat surface 31a of the reflector 3, the reflecting surface 32a having the inclination angle α that is the same as the reflection angle commensurate with the reflected light 72 vertical to the flat surface 31a is provided. By causing ultraviolet ray to enter the reflecting surface 32a at the incident angle that is the same as the inclination angle α, it is possible to control the traveling direction of the reflected light 72 relative to the incident light 71.

Figure 8:
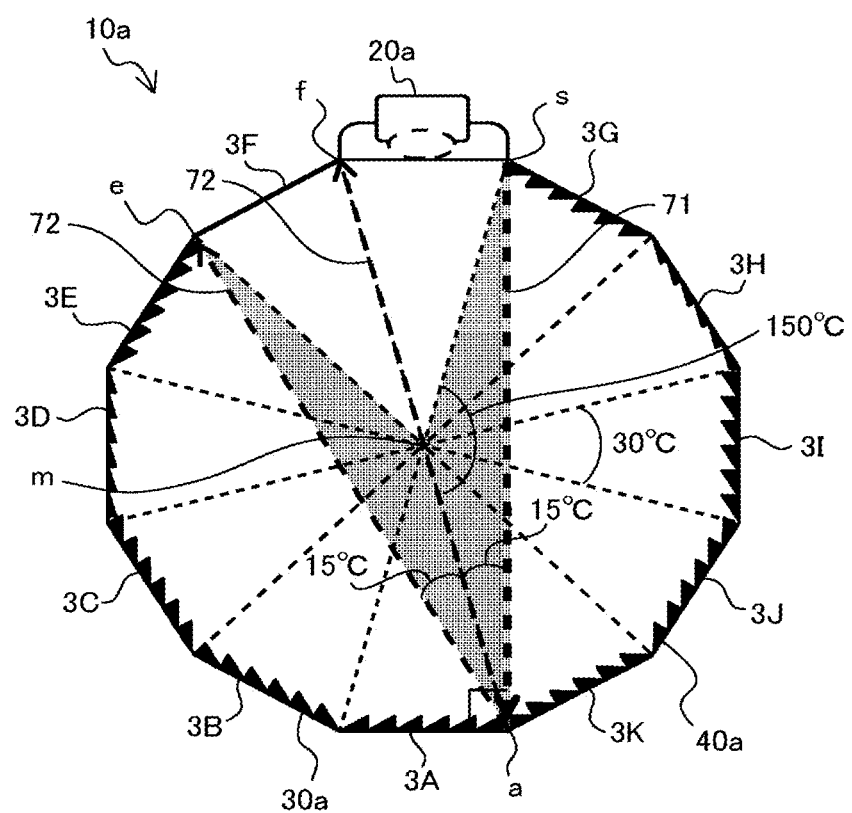
FIG. 8 is a schematic diagram that shows an inclination angle required to reflect ultraviolet ray that has vertically entered the reflector that constitutes one of sides of a polygonal shape that is the cross-sectional shape of a reflecting portion shown in FIG. 3, to the reflector that constitutes a specified one of the sides.

FIG. 8 is a schematic diagram for showing an inclination angle required to reflect ultraviolet ray that has vertically entered the reflector 3 that constitutes one of the sides of the polygonal shape that is the cross-sectional shape of the reflecting portion 30a, to the reflector 3 that constitutes a specified one of the sides. FIG. 8 illustrates a point at which ultraviolet ray is generated as a light flux generating point s, and illustrates a point on the reflector 3A, at which the ultraviolet ray emitted from the light flux generating point s enters and is reflected by the reflector 3A, as a light flux reflecting point a. In FIG. 8, among points that ultraviolet ray reflected at the light flux reflecting point a reaches and is reflected, the point on the reflector 3E is illustrated as a light flux reflecting point e, and the point on the reflector 3F is illustrated as a light flux reflecting point f. In addition, in FIG. 8, the center of the regular dodecagonal shape that is the cross-sectional shape of the reflecting portion 30a is shown as a center portion m. An inclination angle required to reflect ultraviolet ray that has vertically entered certain one of the reflectors 3, to another one of the reflectors 3 will be described with reference to FIG. 8.

Initially, a situation in which ultraviolet ray vertically enters the reflector 3A and is reflected to the reflector 3F that is the fifth reflector in the clockwise direction will be described. As shown in FIG. 8, a triangle formed by connecting the light flux generating point s, the light flux reflecting point a and the center portion m is an isosceles triangle having an angle sma of 150° since a distance between m and s and a distance between m and a are the radius of a circle connecting the vertices of the regular dodecagonal shape. For this reason, the angle mas is 15°.

When ultraviolet ray that has vertically entered the reflector 3A is reflected to the reflector 3F, an angle obtained by adding the incidence angle and the reflection angle with each other needs to be the angle mas, so the incident angle and the reflection angle each are 7.5°. Thus, the ultraviolet sterilizer 10a includes the reflector 3A having the upward-sloping reflecting surface 32a at an inclination angle of 7.5°, so it is possible to reflect ultraviolet ray that has vertically entered the reflector 3A, to the reflector 3F.

Next, the case where ultraviolet ray vertically enters the reflector 3A and is reflected by the fourth reflector 3E in the clockwise direction will be described. As shown in FIG. 8, a triangle that connects the center portion m, the light flux reflecting point a and the light flux reflecting point e is an isosceles triangle having an angle ema of 150° since a distance between m and a and a distance between m and e each are equal to the radius of the circle connecting the vertices of the regular dodecagonal shape. For this reason, the angle mae is calculated as 15°.

When ultraviolet ray that has vertically entered the reflector 3A is reflected to the reflector 3E, the incident angle that is the angle sam and the reflection angle that is the angle mae each are 15°. Thus, by providing the ultraviolet sterilizer 10a with the reflector 3A having the upward-sloping reflecting surfaces 32a at an inclination angle of 15°, it is possible to reflect ultraviolet ray that has vertically entered the reflector 3A, to the reflector 3E.

Figure 9:
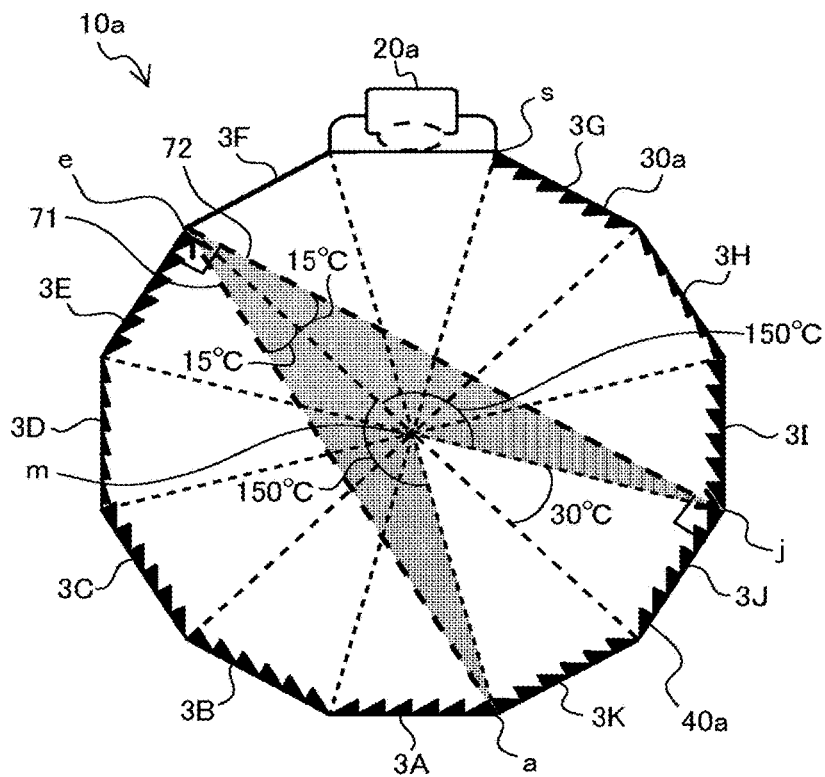
FIG. 9 is a schematic diagram for showing an inclination angle required to vertically reflect ultraviolet ray from the reflector that constitutes one of the sides of the polygonal shape that is the cross-sectional shape of the reflecting portion shown in FIG. 3, to the reflector that constitutes a specified one of the sides.

FIG. 9 is a schematic diagram for showing an inclination angle required to vertically reflect ultraviolet ray from the reflector 3 that constitutes one of the sides of the polygonal shape that is the cross-sectional shape of the reflecting portion 30a, to the reflector 3 that constitutes a specified one of the sides. FIG. 9, as well as FIG. 8, shows the light flux generating point s, the light flux reflecting point a, the light flux reflecting point e and the center portion m. In FIG. 9, a point on the reflector 3J, at which ultraviolet ray that has been reflected at the light flux reflecting point e reaches and is reflected by the reflector 3J, is illustrated as a light flux reflecting point j.

An inclination angle required to vertically reflect ultraviolet ray that has entered a certain one of the reflectors 3, to another one of the reflectors 3 will be described with reference to FIG. 9. A central angle obtained by dividing 360° that is the angle of the center of the regular dodecagonal shape into twelve that is the number of angles of the polygonal shape is 30°. For this reason, in the regular dodecagonal shape, a certain one of the sides and the sixth side from that side in the clockwise direction are definitely parallel to each other and face each other. Thus, when ultraviolet ray is vertically reflected from a certain one of the sides, the reflected ultraviolet ray definitely vertically enters the flat surface 31a of the facing reflector 3 of the regular dodecagonal shape. Therefore, a situation in which ultraviolet ray from the reflector 3A enters the reflector 3E, the entered ultraviolet ray is reflected from the reflector 3E to a direction perpendicular to the flat surface 31a and enters the reflector 3J located at a facing surface in the regular dodecagonal shape will be described with reference to FIG. 9.

As shown in FIG. 9, a triangle obtained by connecting the center portion m, the light flux reflecting point a and the light flux reflecting point e is an isosceles triangle having an angle ema of 150° since a distance between m and a and a distance between m and e each are the radius of a circle obtained by connecting the vertices of the regular dodecagonal shape and are equal to each other. For this reason, the angle aem is calculated as 15°. A triangle obtained by connecting the center portion m, the light flux reflecting point e and the light flux reflecting point j is an isosceles triangle having an angle jme of 150° since a distance between m and e and a distance between m and j each are the radius of a circle having a regular dodecagonal shape as vertices and are equal to each other. For this reason, the angle mej is calculated as 15°.

When ultraviolet ray that has been reflected by the reflector 3A and then vertically reflected by the reflector 3E relative to the flat surface 31a is reflected to the reflector 3J located at a facing surface in the regular dodecagonal shape, the incident angle that is the angle mea and the reflection angle that is the angle mej each are 15°. Thus, by providing the ultraviolet sterilizer 10a with the reflector 3E having the downward-sloping reflecting surfaces 32a at an inclination angle of 15°, it is possible to reflect ultraviolet ray that has been vertically reflected relative to the flat surface 31a of the reflector 3E, to the reflector 3J located at the facing surface of the regular dodecagonal shape.

Based on the above-described method of calculating the angle of each reflecting surface 32a of the reflector 3 relative to the incident angle and the reflection angle, the shape each the reflecting surface 32a of each reflector 3 as described above is prepared as follows in Embodiment 1.

Each of the reflector 3A, the reflector 3G, the reflector 3I and the reflector 3J has a prism shape such that the inclination angle α is 15° and upward sloping.

Each of the reflector 3B, the reflector 3C, the reflector 3E and the reflector 3K has a prism shape such that the inclination angle α is 15° and downward sloping.

The reflector 3D has a prism shape such that the inclination angle α is 7.5° and upward sloping.

The reflector 3H has a prism shape such that the inclination angle α is 7.5° and downward sloping.

The reflector 3F has a flat shape.

With the reflecting portion 30a prepared as described above, starting from a situation in which ultraviolet ray is caused to vertically enter the reflector 3A, the ultraviolet ray is reflected by all the reflectors 3 along the radial direction in order of the reflector 3A, the reflector 3E, the reflector 3J, the reflector 3C, the reflector 3H, the reflector 3D, the reflector 3I, the reflector 3B, the reflector 3G, the reflector 3K and the reflector 3F. Since the surface shape of the reflector 3F is a flat shape, ultraviolet ray that vertically enters from the reflector 3K is totally reflected by the reflector 3F, and is vertically reflected to the reflector 3K. After that, based on the relation between the incident angle and the reflection angle, the ultraviolet ray is reflected in the reverse order, that is, in order of the reflector 3K, the reflector 3G, the reflector 3B, the reflector 3I, the reflector 3D, the reflector 3H, the reflector 3C, the reflector 3J, the reflector 3E and the reflector 3A, and further continues to be reflected along the radial direction.

That is, in the ultraviolet sterilizer 10a, ultraviolet ray that has vertically entered the reflector 3A alternately repeats reflection in the traveling direction indicated by the broken line arrows 7 in FIG. 3 and reflection in the traveling direction reverse to the broken line arrows 7. As a result, as shown in FIG. 3, ultraviolet ray emitted from the emitting portion 20a of the ultraviolet sterilizer 10a is reflected all over the area through which air passes in the ultraviolet sterilizer 10a. In this way, the ultraviolet sterilizer 10a forms a screen-shaped sterilizing light screen based on ultraviolet ray. That is, the ultraviolet sterilizer 10a forms the screen-shaped sterilizing light screen based on ultraviolet ray inside the cylindrical casing 40a, so it is possible to sterilize air all over the area perpendicular to the outflow direction. That is, with the ultraviolet sterilizer 10a, the irradiance of ultraviolet ray inside the cylindrical casing 40a increases as compared to the case where ultraviolet ray is not reflected, so it is possible to obtain high sterilizing effect.

Incidentally, microbes in the air are suspended while being adherent to cough, sputum, dust, or the like; however, inside the ultraviolet sterilizer 10a, ultraviolet ray is reflected at multiple angles, so the shade of a deposit reduces. For this reason, with the ultraviolet sterilizer 10a, ultraviolet ray is emit to further more microbes, and it is possible to efficiently sterilize air.

Figure 10:
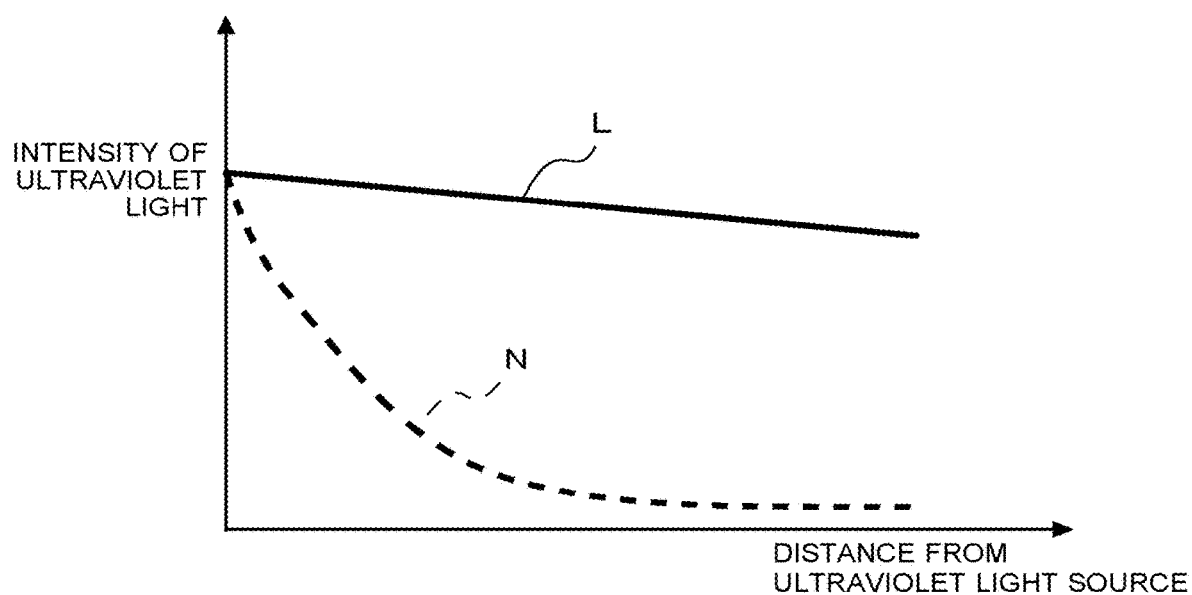
FIG. 10 is a graph that shows the relation between a distance from an emitting portion that is an ultraviolet ray source and an intensity of ultraviolet ray.

FIG. 10 is a graph that shows the relation between a distance from the emitting portion 20a that is the ultraviolet ray source and an intensity of ultraviolet ray. The intensity of light attenuates in accordance with the inverse-square law when light is divergently emitted from a point light source. On the other hand, parallel rays having strong directivity do not diverge and travel with an equal irradiation area, so the intensity is difficult to attenuate.

In this respect, with the ultraviolet sterilizer 10a, since the emitting portion 20a emits ultraviolet ray as parallel rays having strong directivity via the collimate lens, it is possible to reduce attenuation of the intensity of ultraviolet ray as shown by the graph L indicated by the continuous line in FIG. 10. That is, ultraviolet ray that is reflected on the reflectors 3 of the ultraviolet sterilizer 10a just decreases in irradiation intensity due to reflection and travels with almost no attenuation even passing through the air. Thus, ultraviolet ray is emit to the entire inner surface of the reflecting portion 30a of the ultraviolet sterilizer 10a, and the intensity of the ultraviolet ray increases as compared to the intensity at the time of emission in accordance with the number of reflections. As a result, in all the inside of the cylindrical casing 40a of the ultraviolet sterilizer 10a, the intensity of ultraviolet ray increases in accordance with the number of reflections, so it is possible to increase the efficiency of sterilizing microbes contained in the air. If the emitting portion 20a is not equipped with the collimate lens, or the like, the intensity of ultraviolet ray attenuates in accordance with the inverse-square law as shown by the graph N indicated by the broken line in FIG. 10.

FIG. 11 is a table that shows an ultraviolet ray irradiance at the level of 1 mm above each reflector 3 shown in FIG. 3. An increase in ultraviolet ray irradiance due to reflection at each reflector 3 will be specifically described with reference to FIG. 11.

In Embodiment 1, an ultraviolet ray irradiance provided by the ultraviolet sterilizer 10a is defined as the following mathematical expression 1. Here, an ultraviolet ray intensity is a quantity obtained by accumulating the intensity of ultraviolet ray that enters each reflector 3 and the intensity of ultraviolet ray that has been reflected on each of the reflectors 3 in the case where the total radiant flux of ultraviolet ray emitted from the emitting portion 20a has been reflected until the total radiant flux attenuates to 1%. The reflectance of ultraviolet ray is 95%. For example, when the emitting portion 20a emits parallel rays at 0.4 W/cm$^2$ and the area of the emitting portion 20a is 3 cm$^2$ (1 cm×3 cm), the total radiant flux of ultraviolet ray is 1.2 W. When the thickness of the ultraviolet sterilizer 10a in an air course direction is 1 cm, an air velocity caused by the air-sending device 15 is 3 m/s, so an irradiation time is 0.0033 s.

[Math. 1]

$$(\text{Ultraviolet Light Irradiance}) = (\text{Ultraviolet Light Intensity}) \times (\text{Irradiation Time}) \qquad (1)$$

Ultraviolet light emitted from the emitting portion 20a continue to be reflected on the reflectors 3 until the total radiant flux attenuates to 1% or below, and ultraviolet ray is emit all over the cross section of the ultraviolet sterilizer 10a. For this reason, an ultraviolet ray irradiance on each reflector 3 is higher than or equal to 4.5 mW·s/cm$^2$ at each of the reflector 3A, the reflector 3E, the reflector 3J, the reflector 3C, the reflector 3H, the reflector 3D, the reflector 3I, the reflector 3B, the reflector 3G and the reflector 3K, and is higher than or equal to 2.2 mW·s/cm$^2$ at each of the emitting portion 20a and the reflector 3F. Since the emitting portion 20a and the reflector 3F each are a surface on which reflection turns back, the number of reflections is smaller than that of the other reflectors, so an ultraviolet ray irradiance is about half.

Since an accumulated value of irradiances of overlapping rays of ultraviolet ray is an ultraviolet ray irradiance at a portion at which rays of ultraviolet ray from the reflectors 3 to the corresponding reflectors 3 overlap, including the center portion of the ultraviolet sterilizer 10a, an ultraviolet ray irradiance further increases.

As described above, the ultraviolet sterilizer 10a is able to keep the ultraviolet ray irradiance at 2.2 mW·s/cm$^2$ or above over the entire ultraviolet sterilizer 10a with ultraviolet ray emitted from all surfaces corresponding to a regular dodecagonal shape in cross section.

FIG. 12 is a graph that shows the relation between an ultraviolet ray irradiance provided by the ultraviolet sterilizer 10a shown in FIG. 3 and a survival rate (PFU/m$^3$) of airborne influenza virus. In FIG. 12, the ordinate axis represents the survival rate of airborne influenza virus, that is, an infectious influenza virus rate to an initial airborne influenza virus 2.5×10$^5$ PFU/m$^3$. The abscissa axis represents the irradiance of UV-LED light having a wavelength of 254 nm. PFU is an abbreviation of plaque forming unit.

As shown in FIG. 12, airborne influenza virus exponentially decreases in survival rate with an increase in ultraviolet ray irradiance. For example, the survival rate of airborne influenza virus is 0.01 at an ultraviolet ray irradiance of 2 mW·s/cm$^2$. That is, when ultraviolet ray having a wavelength of 254 nm is emit to airborne influenza virus at 2 mW·s/cm$^2$, it is possible to deactivate 99% of the airborne influenza virus.

In this respect, the ultraviolet sterilizer 10a is able to keep the ultraviolet ray irradiance at 2 mW·s/cm$^2$ or above in all the area in the cross section inside the ultraviolet sterilizer 10a with only the total radiant flux 1.2 W of ultraviolet ray emitted from the emitting portion 20a. It is possible to deactivate 99% of airborne influenza virus at 2 mW·s/cm$^2$ or above. That is, with the ultraviolet sterilizer 10a, it is possible to increase the irradiance of ultraviolet ray inside the cylindrical casing 40a as compared to when ultraviolet ray is not reflected, so a high sterilizing effect is obtained.

That is, different from the ultraviolet sterilizer 10a, in the case of the existing ultraviolet sterilizer that does not reflect ultraviolet ray, ultraviolet ray emitted from the emitting portion is not reflected, so the ultraviolet ray is emit to only the center portion (about 13% of the cross section) of the ultraviolet sterilizer. That is, with the ultraviolet sterilizer 10a, in comparison with the case where ultraviolet ray is not reflected, it is possible to increase the irradiance of ultraviolet ray in all the space inside the cylindrical casing 40a, so a high sterilizing effect is obtained.

As described above, the ultraviolet sterilizer 10a according to Embodiment 1 reflects ultraviolet ray in all over the area in the cross section of the ultraviolet sterilizer 10a, so it is possible to increase the irradiance of ultraviolet ray. For this reason, by causing airborne microbes in the air to pass through the ultraviolet sterilizer 10a, it is possible to efficiently sterilize the air.

Since the existing ultraviolet sterilizer is configured such that only parts of the sides are open, there is a problem that installation of the ultraviolet sterilizer in a duct or an air-conditioning apparatus causes a high pressure loss due to the ultraviolet sterilizer and, as a result, the ultraviolet sterilizer is not applicable to the air-conditioning apparatus. In this respect, since the ultraviolet sterilizer 10a is configured such that the sides of the cylindrical casing 40a are open through the inlet port 5 and the outlet port 6, installation of the ultraviolet sterilizer 10a in various devices does not increase a pressure loss.

That is, since the ultraviolet sterilizer 10a is configured such that the entire areas of the sides of the cylindrical casing 40a are open and an opening area relative to the air flow direction Da is large, it is possible to prevent an increase in pressure loss resulting from installation of the ultraviolet sterilizer in various devices. Thus, the ultraviolet sterilizer 10a is allowed to be suitably mounted in a duct or an air-conditioning apparatus.

In addition, since the emitting portion 20a and reflectors 3 of the ultraviolet sterilizer 10a are disposed such that ultraviolet ray is emitted or reflected vertically relative to the air flow direction Da, the optical axis of the ultraviolet ray is emitted or reflected vertically relative to the air flow direction Da, as shown in FIG. 2. Therefore, even with a casing of which the sides are open, like the cylindrical casing 40a, ultraviolet ray emitted from the emitting portion 20a is not reflected to the outside of the ultraviolet sterilizer 10a relative to the air flow direction Da, and it is not necessary to consider the degradation of members or the influence on a human body due to leakage of ultraviolet ray.

In addition, since the thickness d of the ultraviolet sterilizer 10a in the air flow direction Da is reduced, an ultraviolet ray irradiation distance in the air flow direction Da is not extended unlike the ultraviolet sterilizer of Patent Literature 2, so it is possible to prevent an increase in the size of a device, and the ultraviolet sterilizer 10a is suitably applicable to an air-conditioning apparatus, and other devices. In this way, with the ultraviolet sterilizer 10a that allows compact design, it is possible to efficiently perform sterilization with a short distance and to reduce the size of a device to be mounted.

[Installation Method]

A method of installing the ultraviolet sterilizer 10a inside the casing 12 of the air-conditioning apparatus 11a will be described. As shown in FIG. 3 and FIG. 4, since the reflectors 3 of the ultraviolet sterilizer 10a have a prism shape, dust, or other substances, suspended in the air can collide with and adhere to the prism-shaped cross section end of the reflecting portion 30a at the inlet port 5 side. For this reason, the prism-shaped cross section end of the reflecting portion 30a at the inlet port 5 side is desirably treated with soil-resistant coating. For example, a coating using a paint containing modified polyvinyl alcohol and a crosslinking agent, a coating using a paint containing carboxymethyl-cellulose, polyethylene glycol and a crosslinking agent, or other coatings, may be employed as the soil-resistant coating.

[Ultraviolet Light Source]

FIG. 13 is a table that shows an energy (eV), a sterilizing effect and a sterilizing effect per 1 eV by wavelength where a plurality of wavelengths of ultraviolet ray is set in the range of 200 nm to 360 nm. The emitting portion 20a that is the ultraviolet ray source will be described with reference to FIG. 13.

Initially, the wavelength range of ultraviolet ray will be described. Light is a kind of electromagnetic wave, and has an energy. The energy is calculated from the following mathematical expression 1.

[Math. 2]
$$E = hv = h\frac{c}{\lambda} \qquad (2)$$

In the mathematical expression 1, E is the energy of ultraviolet ray, h is a Planck constant (6.63×10−34 J·s=4.1× 10−15 eV·s), v is the frequency of the ultraviolet ray, c is the velocity of light (3.0×108 m/s), and λ is the wavelength of the ultraviolet ray. FIG. 13 shows an energy E by wavelength in the range of 200 nm to 360 nm. As the wavelength λ increases, an energy per one electron reduces.

Incidentally, ultraviolet ray having a wavelength of 200 nm to 360 nm takes a proliferating ability by acting on nucleic acid that is the protoplasm of bacteria to inhibit replication of DNA, thus sterilizing microbes. Ultraviolet light having a wavelength of 200 nm to 360 nm kills bacteria by destroying proteins, and other substances, that are formative substances of cytoplasm and cell membranes, thus sterilizing microbes. According to FIG. 13 that shows a sterilizing effect by wavelength in the range of 200 nm to 360 nm, a range near a wavelength of 260 nm has the highest sterilizing effect.

When the sterilizing effect per 1 eV of each wavelength increases, it is recognized that sterilization is efficiently performed. That is, although the wavelength range of ultraviolet ray having the effect of sterilizing microbes is 200 nm to 360 nm, ultraviolet ray having a wavelength of 200 nm to 360 nm may be used as the ultraviolet ray that the emitting portion 20a emits. Desirably, the emitting portion 20a should be configured to emit ultraviolet ray that has a wavelength of 200 nm to 300 nm and that provides a relatively high sterilizing effect. More desirably, the emitting portion 20a should be configured to emit ultraviolet ray that has a wavelength of 240 nm to 290 nm and that is able to efficiently perform sterilization while reducing a consumption energy.

[Ultraviolet Light Emitting Element]

Next, the ultraviolet ray emitting element of the emitting portion 20a will be described. An ultraviolet ray emitting diode (ultraviolet LED) configured to emit ultraviolet ray that has a wavelength of 200 nm to 360 nm and that provides the effect of sterilizing microbes may be used as the ultraviolet ray emitting element. More desirably, the wavelength of ultraviolet ray that the ultraviolet ray emitting element emits should be 240 nm to 290 nm.

The emitting portion 20a that is the ultraviolet ray source has a structure configured to emit parallel rays having strong directivity in addition to the ultraviolet ray emitting element as an ultraviolet ray emitter. In Embodiment 1, the structure that the collimate lens is disposed inside the ultraviolet ray emitting element is employed as the structure configured to emit parallel rays having strong directivity; however, the structure configured to emit parallel rays having strong directivity is not limited to this structure. Instead of the collimate lens, for example, a Fresnel lens may be provided. The emitting portion 20a may have a structure such that a reflector is provided behind a light source.

The ultraviolet ray emitting element, the collimate lens, and other components, may be packaged or modularized as the ultraviolet ray source. By packaging or modularizing the ultraviolet ray emitting element, the collimate lens, and other components, simple installation of the emitting portion 20a is possible.

One or more ultraviolet ray emitting elements are disposed so as to be able to emit parallel rays of ultraviolet ray from the entire surface defined by the sides along the air flow direction Da and one of the sides of the regular dodecagonal shape that is the cross-sectional shape, in the reflecting portion 30a at which the emitting portion 20a is installed.

[Method of Preparing Reflectors]

Next, a method of preparing the reflectors 3 of which the surface has a prism shape will be described.

Initially, the prism shape of each reflector 3 will be described. An average pitch Ap that is the length of the flat surface of each right-angled triangle in the prism shape shown in FIG. 4 just needs to be 0.01 mm to 10 mm, and desirably 0.1 mm to 10 mm.

Subsequently, the base material of each reflector 3 will be described. An ultraviolet ray reflecting material means, for example, a material having a reflectance of 40% or above, desirably, 60% or above and, more desirably, 70% or above on, for example, ultraviolet ray having a wavelength of 250 nm to 270 nm, particularly, ultraviolet ray of 265 nm. Examples of the ultraviolet ray reflecting material that may be suitably used in the invention include chromium (ultraviolet ray reflectance: about 50%), platinum (ultraviolet ray reflectance: about 50%), rhodium (ultraviolet ray reflectance: about 65%), magnesium carbonate (ultraviolet ray reflectance: about 75%), calcium carbonate (ultraviolet ray reflectance: about 75%), magnesia oxide (ultraviolet ray reflectance: about 90%) and aluminum (ultraviolet ray reflectance: about 90%). Additionally, when a surface treatment, such as an electroplating method and a vapor deposition method, is applied to these ultraviolet ray reflecting materials, the surface has a high reflectance.

Since aluminum is excellent in workability, aluminum may be suitably used as the ultraviolet ray reflecting material. By further coating aluminum with magnesium fluoride $MgF_2$ as a surface treatment for aluminum, it is possible to protect the surface of the aluminum material and increase the reflectance in the ultraviolet range.

Subsequently, a method of molding each reflector 3 of which the surface has a prism shape will be described. Initially, a die having the shape of the reflector 3 is prepared. A material plate for the reflector 3, cut into a length approximately equal to the thickness d of the cylindrical casing 40a in the air flow direction Da is put on the prepared die, the put material plate is worked by mechanical bending, such as hand bending, pressing, roll bender and roll forming. The worked material plate is bent into a polyhedral shape. Thus, the reflecting portion 30a is formed. Each reflector 3 may be formed by cutting and working a metal plate having a thickness larger than an average depth.

Furthermore, each reflector 3 may be prepared as follows. A base having the same shape as the reflector 3 is molded by using a material other than the above-described metals, and then metal powder paste is evaporated onto the surface of the base. In this case, a die having the shape of the reflector 3 is prepared, and a member that corresponds to the base may be formed by using a resin material by press working, injection molding, compression molding, or the like. After that, metal powder paste that becomes a reflecting material is evaporated onto the surface layer of the base, thus forming the reflector 3. In this way, when the reflector 3 is formed by using a combination of a resin material and evaporation of metal powder paste, it is advantageous in that material cost is reduced as compared to when a metal plate is used and this combination is easier to be molded than the metal material.

A thermoplastic resin, such as polyethylene (PE), polypropylene (PP), polyvinyl chloride (PVC), polyethylene terephthalate (PET) and ABS resin, may be used as a resin material for molding a base. The base of each reflector 3 may be molded by using a thermosetting resin, such as phenolic resin, amino resin, epoxy resin and urethane resin, synthetic rubber, such as polyisoprene and butadiene, and synthetic fiber, such as nylon, vinylon, acrylic fiber and rayon, that are plastic materials other than the above.

In Embodiment 1, the case where the cross-sectional shape of the ultraviolet sterilizer 10a, that is, the front view when viewed from the inlet port 5 side in the axial longitudinal direction of the cylindrical casing 40a, is a regular dodecagonal shape is described; however, the cross-sectional shape of the ultraviolet sterilizer 10a is not limited to this. As long as the reflectors 3 are disposed and the reflecting surfaces 32a are worked such that ultraviolet ray is reflected all over the area in the cross section of the ultraviolet sterilizer 10a, that is, ultraviolet ray is reflected along the radial direction of the cylindrical casing 40a, the cross-sectional shape of the ultraviolet sterilizer 10a may be a regular polygonal shape having the different number of vertices, a polygonal shape with sides having different lengths or a polygonal shape in which interior angles are freely set.

The shape in which right-angled triangles having a hypotenuse inclined at the inclination angle $\alpha$ relative to the flat part 31 are arranged side by side is illustrated as the prism shape of the surface of each reflector 3; however, the prism shape is not limited to this shape. As long as a shape allows ultraviolet ray to be reflected to the intended reflector 3, another shape may be employed. In addition, in Embodiment 1, the case where the reflecting part 32 of each reflector 3 is the prism shape is illustrated; however, the reflecting part 32 is not limited to this shape. The reflecting surfaces 32a of each reflecting part 32 each may be formed so as to be inclined at a set angle relative to the flat surface 31a of the flat part 31. That is, the cross-sectional shape of the reflecting part 32 may be a single right-angled triangular shape having a hypotenuse inclined at the inclination angle $\alpha$ relative to the flat part 31.

In Embodiment 1, the ultraviolet sterilizer 10a in which the single emitting portion 20a is installed at the outer peripheral portion is illustrated; however, the ultraviolet sterilizer 10a is not limited to this. The ultraviolet sterilizer 10a may be configured such that a plurality of emitting portions 20a is installed. In this case, the emitting portions 20a just need to be installed at certain intervals. In this way, when the plurality of emitting portions 20a is installed in the ultraviolet sterilizer 10a, the outgoing strength increases, so it is possible to increase the sterilizing effect. In Embodiment 1, the structure that the emitting portion 20a vertically emits ultraviolet ray to the facing reflector 3 is described. As long as the prism shape of each reflector 3 is able to be designed such that ultraviolet ray is repeatedly reflected inside the cylindrical casing 40a, the emitting portion 20a may be configured to emit ultraviolet ray to the reflector 3 other than the reflector 3A. In addition, the air-sending device 15 may be arranged inside the casing 12.

Example

Figure 14:
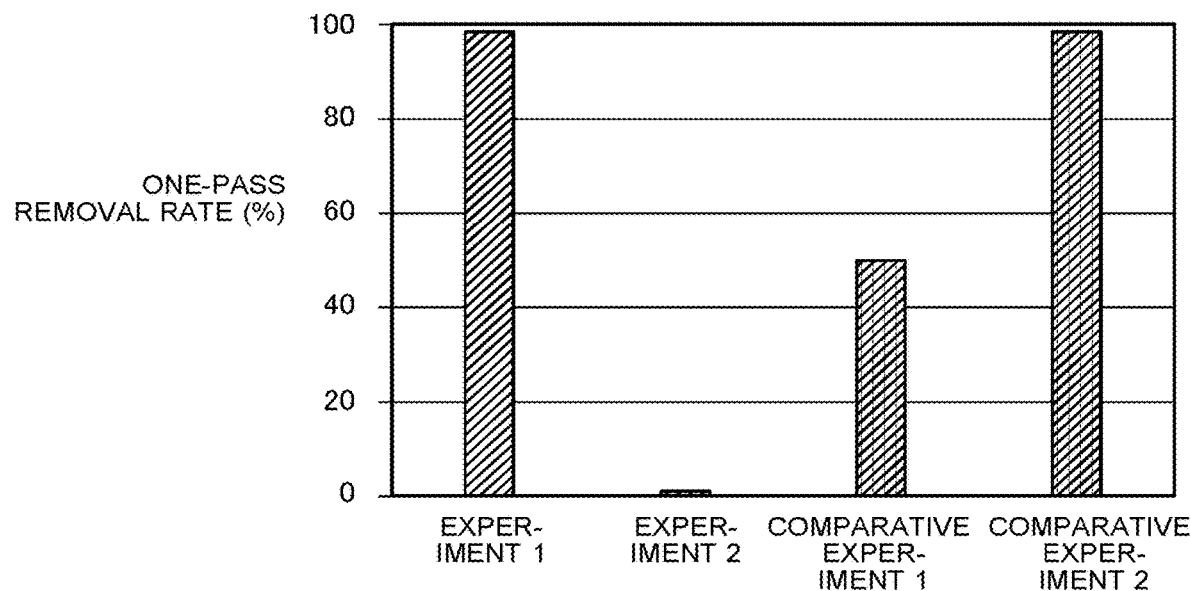
FIG. 14 is a graph that shows sterilizing effects as experimental results of an example according to Embodiment 1 of the present invention.
Figure 15:
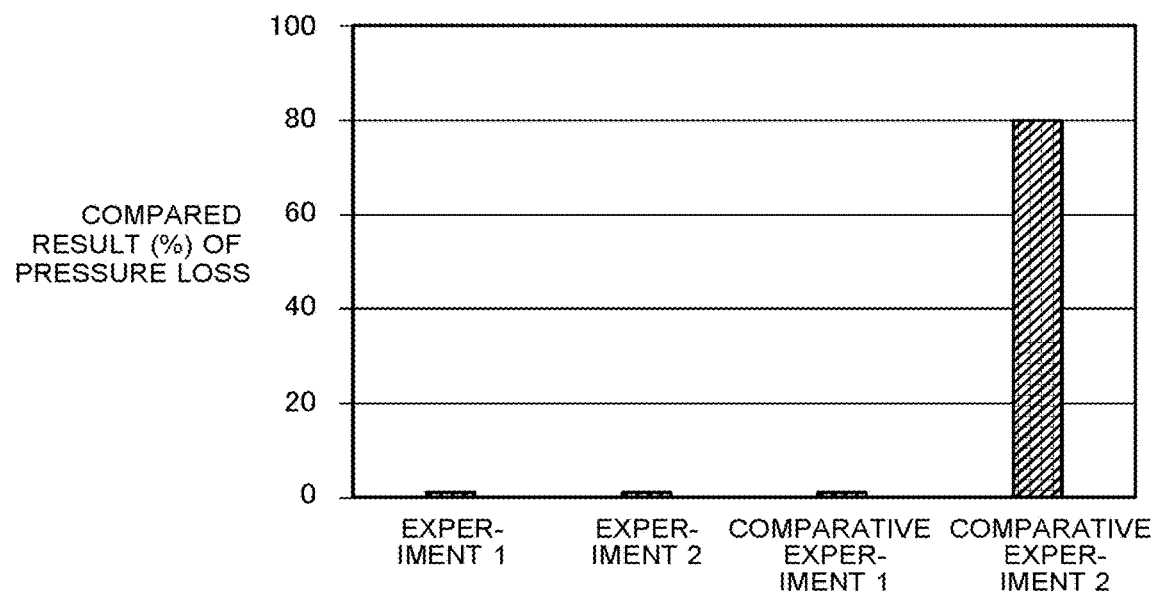
FIG. 15 is a graph that shows pressure losses as experimental results of the example according to Embodiment 1 of the present invention.

FIG. 14 is a graph that shows sterilizing effects as the experimental results of an example according to Embodiment 1. FIG. 15 is a graph that shows pressure losses as experimental results of the example according to Embodiment 1. In the present example, to examine the sterilizing effect for microbes, *staphylococcus* epidermidis was suspended in the air of the inlet port 5 by spraying *staphylococcus* epidermidis into the air, and then a temporal change in the survival rate of *staphylococcus* epidermidis in each of Experiment 1, Experiment 2, Comparative Experiment 1 and Comparative Experiment 2 with different experimental conditions was investigated.

In each experiment, the diameter of the casing 12 was set to 100 mm, and the velocity of flow of air was set to 3 m/s. An ultraviolet diode that is able to emit ultraviolet ray having a wavelength of 254 nm in parallel rays at an irradiation intensity of 0.01 W/cm$^2$ to 5.0 W/cm$^2$ was used as the emitting portion 20a that is the ultraviolet ray source. The ultraviolet diode that serves as the emitting portion 20a desirably emits ultraviolet ray at an irradiation intensity of 0.04 W/cm$^2$. In addition, a regular dodecagonal aluminum plate having an average pitch Ap of 1 mm was used as each reflector 3. The ultraviolet sterilizer 10a having a thickness d of 1 cm in the air flow direction Da was used. *Staphylococcus epidermidis* was sprayed by nebulizer into the air, and the number of bacteria in the air at the inlet port 5 was adjusted to $10^5$ CFU (Colony Forming Unit)/cm$^3$.

Experiment 1 was carried out under the experimental condition that the ultraviolet sterilizer 10a is installed in the casing 12 and is operated. Experiment 2 was carried out under the experimental condition that the ultraviolet sterilizer 10a is installed in the casing 12 and is stopped. Comparative Experiment 1 was carried out under the experimental condition that the ultraviolet sterilizer 10a in which no reflector 3 is installed is installed in the casing 12 and is operated. Comparative Experiment 2 was carried out under the experimental condition that the ultraviolet sterilizer 10a in which the opening area of the inlet port 5 and the opening area of the outlet port 6 are narrowed to 10% is installed in the casing 12 and is operated.

The ordinate axis of FIG. 14 represents a one-pass removal rate that is the removal rate of bacteria in the air at the time when air has passed through the ultraviolet sterilizer 10a once. That is, the one-pass removal rate is a value obtained by dividing a value obtained by subtracting the number of bacteria in the effluent air from the number of bacteria in the influent air, by the number of bacteria in the influent air. The ordinate axis of FIG. 15 represents a comparative result of pressure loss at the time when air passes through the ultraviolet sterilizer 10a. That is, in FIG. 15, the proportions (%) of pressure losses in the other Experiments with reference to the pressure loss in Experiment 1 are shown.

In Experiment 1, the pressure loss did not increase, and the number of bacteria was able to be reduced by 99%. However, in Experiment 2, the pressure loss did not increase, but the number of bacteria was just reduced by 1%. In Comparative Experiment 1, the pressure loss did not increase, but the number of bacteria was just reduced by 50%. In Comparative Experiment 2, the number of bacteria was able to be reduced by 99%, but the pressure loss was high.

From the above, it is understood that, only in the case of Experiment 1, there was no pressure loss and sterilization was efficiently performed. In Experiment 2 and Comparative Experiment 1, although the pressure losses did not increase, but the rates of sterilization were lower than that in the case of Experiment 1. In Comparative Experiment 2, the rate of sterilization was high, but the pressure loss was high and the air-sending device 15 stopped along the way.

From these results, with the experimental condition of Experiment 1 in which sterilization is performed by the ultraviolet sterilizer 10a, it is possible to efficiently perform sterilization at the one-pass removal rate of 99% without increasing the pressure loss. That is, even when the ultraviolet sterilizer 10a in Embodiment 1 is mounted on the air-conditioning apparatus 11a, the ultraviolet sterilizer 10a is able to perform efficient sterilization without increasing the pressure loss.

<Alternative Embodiment>

Figure 16:
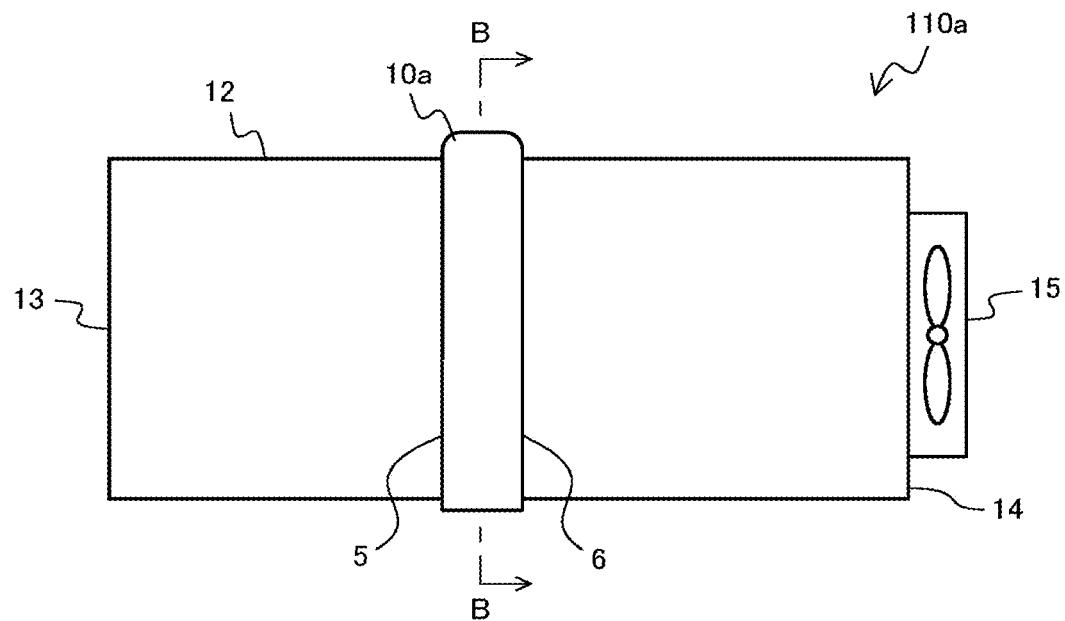
FIG. 16 is a schematic diagram that shows the schematic configuration of an air-conditioning apparatus according to an alternative embodiment to Embodiment 1 of the present invention.
Figure 17:
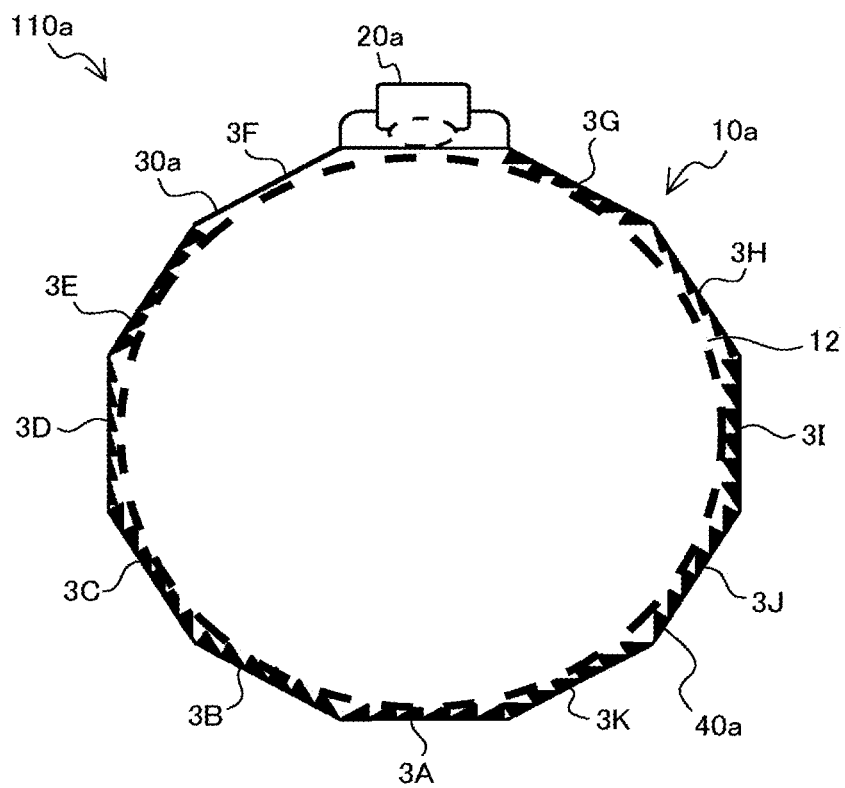
FIG. 17 is a schematic cross-sectional view of the air-conditioning apparatus, taken along the line B-B in FIG. 16.

FIG. 16 is a schematic diagram that shows the schematic configuration of an air-conditioning apparatus according to an alternative embodiment to Embodiment 1 of the present invention. FIG. 17 is a schematic cross-sectional view of the air-conditioning apparatus, taken along the line B-B in FIG. 16. The ultraviolet sterilizer 10a is configured such that the entire areas of the sides of the cylindrical casing 40a are open as described above. In the alternative embodiment, as shown in FIG. 16 and FIG. 17, the inside diameter of the inlet port 5 is larger than or equal to the inside diameter of the air intake 13, and the inside diameter of the outlet port 6 is larger than or equal to the inside diameter of the outlet opening 14. Thus, the ultraviolet sterilizer 10a of the alternative embodiment is further suitably mounted in a duct or the air-conditioning apparatus.

The air-conditioning apparatus 110a of the alternative embodiment is configured such that the inside diameter of the reflecting portion 30a of the ultraviolet sterilizer 10a is larger than or equal to the outside diameter of the casing 12. That is, since the air-conditioning apparatus 110a is configured such that the protrusions of the prism shape of each reflector 3 do not project into the air course of the casing 12, there is a low possibility that dust, or other substances, suspended in the air collide with and adhere to the prism-shaped cross section end of the reflecting portion 30a at the inlet port 5 side. For this reason, with the air-conditioning apparatus 110a, it is possible to reduce adhesion of dust, or other substances, to the prism-shaped cross section end of the reflecting portion 30a at the inlet port 5 side without applying soil-resistant coating to the cross section end. In addition, with the air-conditioning apparatus 110a, since air does not collide with the prism-shaped cross section end of the reflecting portion 30a at the inlet port 5 side, it is possible to reduce the pressure loss. The air-conditioning apparatus 110a may also be configured such that at least part of the protrusions of the prism shape of each reflector 3 do not project into the air course of the casing 12.

Embodiment 2

Figure 18:
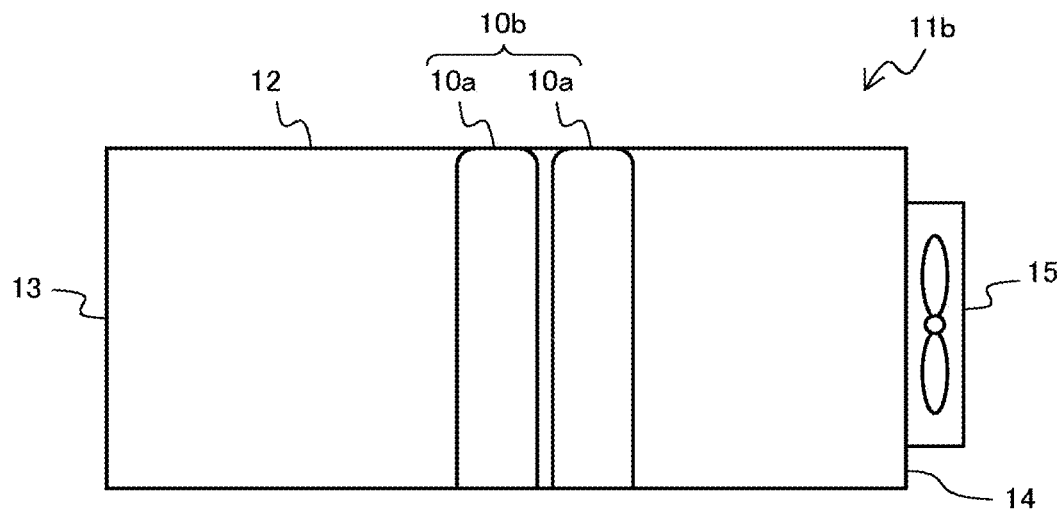
FIG. 18 is a schematic diagram that shows the schematic configuration of an air-conditioning apparatus according to Embodiment 2 of the present invention.
Figure 19:
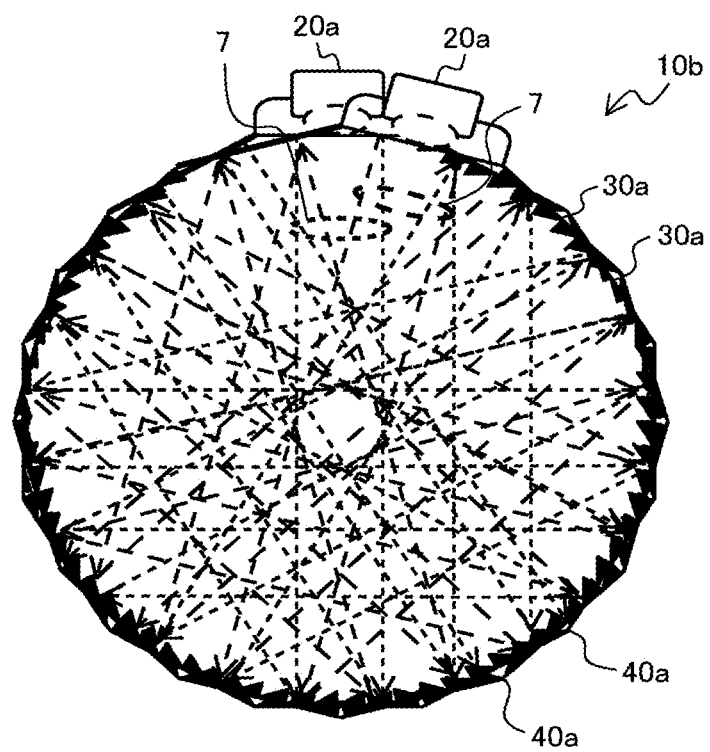
FIG. 19 is a diagram that shows the schematic cross sections of two ultraviolet sterilizers according to Embodiment 2 of the present invention in layers.

FIG. 18 is a schematic diagram that shows the schematic configuration of an air-conditioning apparatus according to Embodiment 2. FIG. 19 is a diagram that shows the schematic cross sections of two ultraviolet sterilizers according to Embodiment 2 in layers. As shown in FIG. 18, the air-conditioning apparatus 11b according to Embodiment 2 includes the two ultraviolet sterilizers 10a disposed in parallel between the air intake 13 and the outlet opening 14 as an ultraviolet sterilizer 10b. That is, the air-conditioning apparatus 11b has similar components to the components in the above-described Embodiment 1 except that the two ultraviolet sterilizers 10a are installed in the air flow direction Da. Thus, like reference numerals denote equivalent constituent members to those of the ultraviolet sterilizer 10a and the air-conditioning apparatus 11a in Embodiment 1, and the description is omitted.

The centers of the two ultraviolet sterilizers 10a in the outflow direction agree with each other, and the positions of the emitting portions 20a of the two ultraviolet sterilizers 10a are different in the outflow direction. More specifically, as shown in FIG. 19, in the ultraviolet sterilizer 10b, the positions of the emitting portions 20a of the two ultraviolet sterilizers 10a are shifted by 15° about the center of the regular dodecagonal shape that is the cross-sectional shape of each reflecting portion 30a. That is, one of the ultraviolet sterilizers 10a is disposed in a state rotated by 15° about the center relative to the other one of the ultraviolet sterilizers 10a. As a result, as shown in FIG. 19, the optical axis of ultraviolet ray that is generated in each ultraviolet sterilizer 10a is not parallel to each other and does not overlap each other. That is, in the air-conditioning apparatus 11b, the direction of ultraviolet ray that is emit to microbes suspended in the air is twice as many as that of the air-conditioning apparatus 11a in Embodiment 1, so the possibility that airborne microbes are hidden by deposits further decreases. For this reason, with the air-conditioning apparatus 11b, it is possible to further improve sterilizing efficiency.

In Embodiment 2, the case where the two ultraviolet sterilizers 10a are installed in parallel is described; however, the configuration is not limited to this. The air-conditioning apparatus 11b may include three or more ultraviolet sterilizers 10a as the ultraviolet sterilizer 10b. The ultraviolet sterilizers 10a just need to be disposed such that the positions of the emitting portions 20a in the outflow direction are shifted from one another. With this configuration, the direction of ultraviolet ray that is emit to airborne microbes further increases, and the possibility that airborne microbes are hidden by deposits further decreases, so it is possible to further improve sterilizing efficiency.

Embodiment 3

Figure 20:
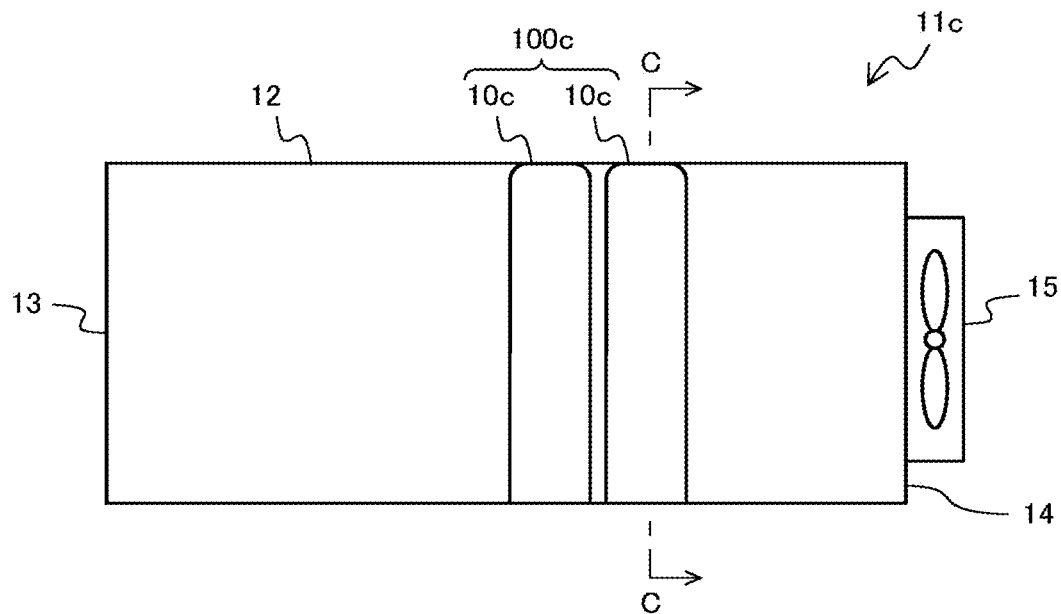
FIG. 20 is a schematic diagram that shows the schematic configuration of an air-conditioning apparatus according to Embodiment 3 of the present invention.
Figure 21:
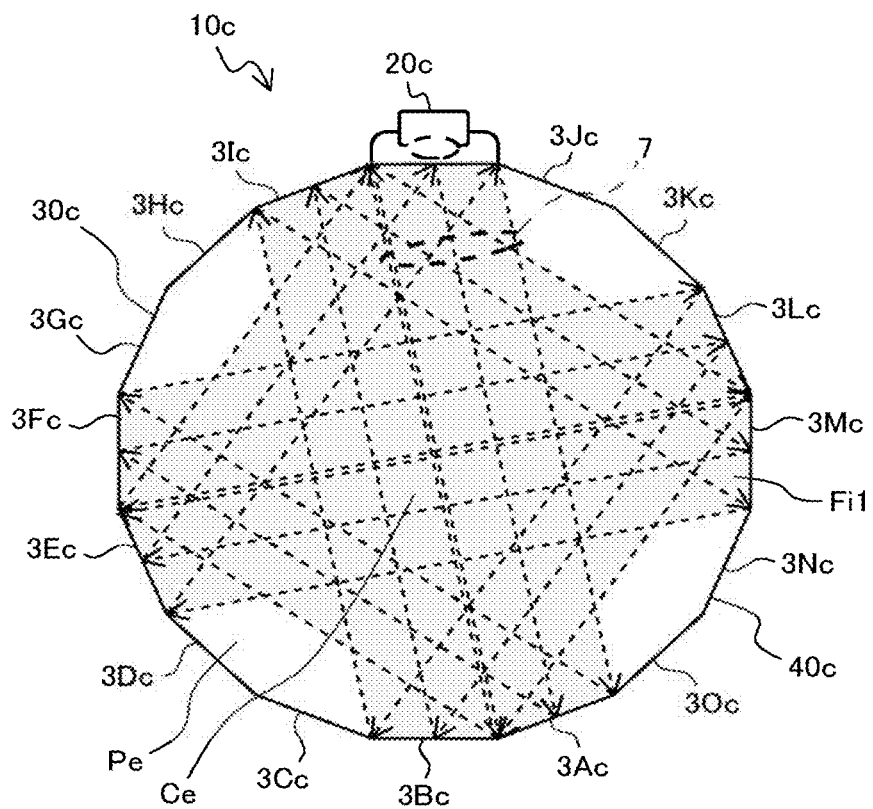
FIG. 21 is a diagram that shows a path along which ultraviolet ray travels in the schematic cross-sectional view of each ultraviolet sterilizer, taken along the line C-C in FIG. 20.
Figure 22:
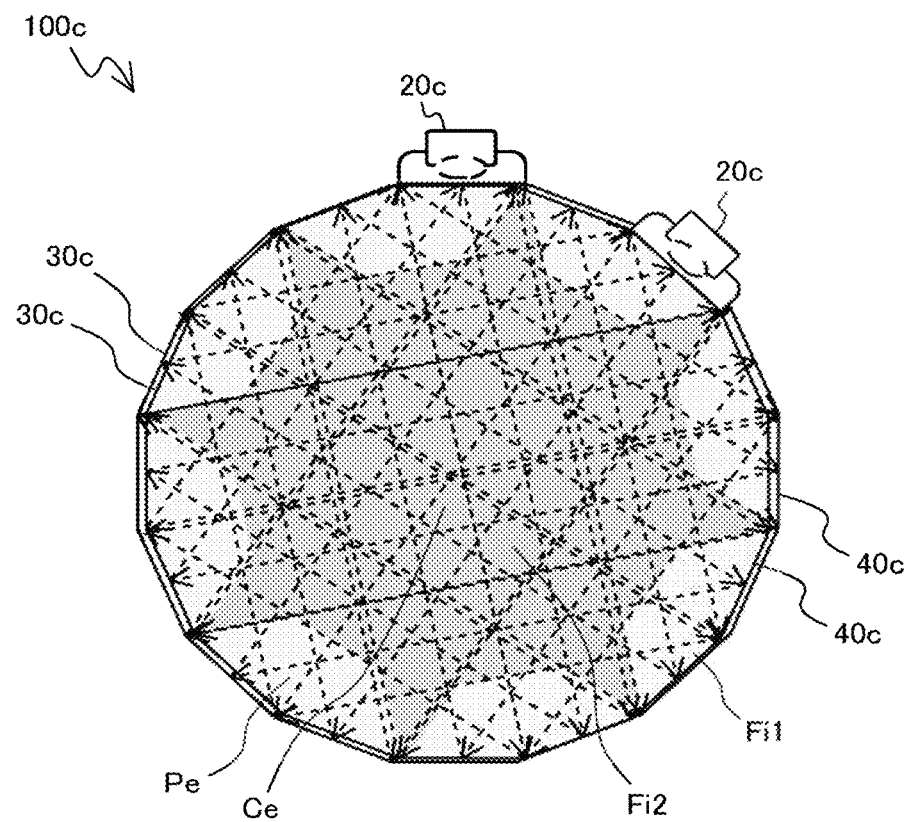
FIG. 22 is a diagram that shows the schematic cross sections of the two ultraviolet sterilizers according to Embodiment 3 of the present invention in layers.
Figure 23:
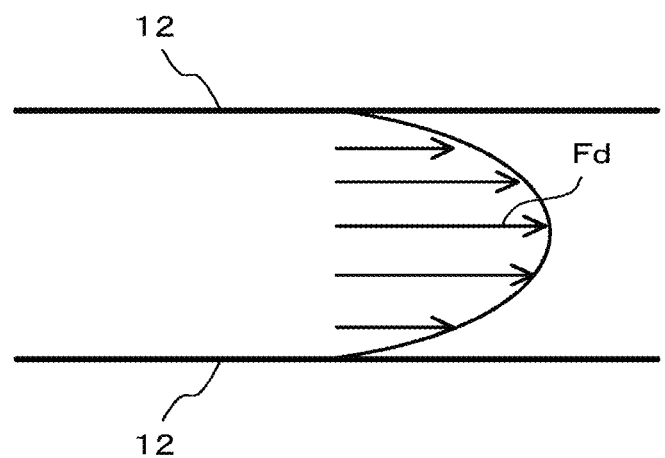
FIG. 23 is a schematic diagram that shows a velocity distribution of air in an air course.

FIG. 20 is a schematic diagram that shows the schematic configuration of an air-conditioning apparatus according to Embodiment 3. FIG. 21 is a diagram that shows a path along which ultraviolet ray travels in the schematic cross-sectional view of each ultraviolet sterilizer, taken along the line C-C in FIG. 20. FIG. 22 is a diagram that shows the schematic cross sections of the two ultraviolet sterilizers according to Embodiment 3 in layers. FIG. 23 is a schematic view that shows a velocity distribution of air in an air course.

As shown in FIG. 21 and FIG. 22, each ultraviolet sterilizer 10c includes a reflecting portion 30c of which the cross-sectional shape that is a front view when viewed from the inlet port 5 side in the axial longitudinal direction of a cylindrical casing 40c is a regular hexadecagonal shape. The reflecting portion 30c includes the reflectors 3 that constitute the sides of the regular hexadecagonal shape. Excepting the above point, each ultraviolet sterilizer 10c is similar to the ultraviolet sterilizer 10a of the above-described Embodiment 1 and Embodiment 2. In the air-conditioning apparatus 11c, the two ultraviolet sterilizers 10c are disposed in parallel in the casing 12, and an emitting portion 20c that is the ultraviolet ray source of one of the ultraviolet sterilizers 10c is disposed in a state inclined by 45° relative to an emitting portion 20c of the other one of the ultraviolet sterilizers 10c. Excepting the above point, the air-conditioning apparatus 11c is similar to the air-conditioning apparatus 11b according to the above-described Embodiment 2. Thus, like reference numerals denote equivalent constituent members to those of Embodiment 1 and Embodiment 2, and the description is omitted.

As shown in FIG. 20, the air-conditioning apparatus 11c according to Embodiment 3 includes the two ultraviolet sterilizers 10c disposed in parallel between the air intake 13 and the outlet opening 14 as an ultraviolet sterilizer 100c.

As shown in FIG. 21, each ultraviolet sterilizer 10c includes the cylindrical casing 40c, the emitting portion 20c and the reflecting portion 30c. The cylindrical casing 40c has a regular hexadecagonal shape as the cross-sectional shape that is the front view when viewed from the inlet port 5 side in the axial longitudinal direction of the cylindrical casing 40c. The emitting portion 20c is disposed at the outer peripheral portion of the cylindrical casing 40c. The reflecting portion 30c is disposed on the inner surface of the cylindrical casing 40c. The cross-sectional shape of the reflecting portion 30c is a regular hexadecagonal annular shape. The emitting portion 20c is provided at one of the sides of the regular hexadecagonal shape that is the cross-sectional shape of the reflecting portion 30c. The emitting portion 20c is an ultraviolet ray emitter including an ultraviolet ray emitting element and a collimate lens.

The reflecting portion 30d includes a plurality of reflectors 3Ac to 3Oc that reflect ultraviolet ray. The reflectors 3Ac to 3Oc respectively constitute the sides of the regular hexadecagonal shape that is the cross-sectional shape of the reflecting portion 30c. Hereinafter, the reflectors 3Ac to 3Oc are also simply collectively referred to as the reflectors 3 or any one of the reflectors 3Ac to 3Oc is also simply referred to as the reflector 3.

The reflector 3Ac is provided on the right side next to the reflector 3Bc facing the emitting portion 20c. The reflectors 3Bc to 3Oc are provided in the clockwise direction from the reflector 3Ac. The emitting portion 20c emits ultraviolet ray toward the reflector 3Ac.

The traveling direction of ultraviolet ray emitted from the emitting portion 20c in the cross section direction of the cylindrical casing 40c will be described with reference to FIG. 21. FIG. 21 shows one of the two ultraviolet sterilizers 10c that constitute the ultraviolet sterilizer 100c.

The surface shape of each of the reflectors 3 that constitute the regular hexadecagonal shape that is the cross-sectional shape, that is, the front view when viewed from the inlet port 5 side in the axial longitudinal direction of the cylindrical casing 40c, is prepared as follows based on the principles of the incident angle and reflection angle of light in consideration of the inclinations of the incident light 71 and reflected light 72 relative to the flat part 31 and the reflecting part 32, as in the case of Embodiment 1.

The surface shape of each of the reflector 3Ac, the reflector 3Ec, the reflector 3Lc and the reflector 3Ic is a prism shape such that the inclination angle α is 11.25° and upward sloping.

The surface shape of each of the reflector 3Bc, the reflector 3Fc and the reflector 3Mc is a prism shape such that the inclination angle α is 11.25° and downward sloping.

The surface shape of the light source-side reflector of the emitting portion 20c, as well as the surface shape of each of the reflector 3Bc, the reflector 3Fc and the reflector 3Mc, is a prism shape such that the inclination angle α is 11.25° and downward sloping.

Each ultraviolet sterilizer 10c includes the reflecting portion 30c having the above-described reflectors 3, and causes ultraviolet ray to enter the seventh reflector 3Ac in the clockwise direction from the emitting portion 20c at 22.5°. The ultraviolet ray emitted from the emitting portion 20c and reflected on the reflector 3Ac is reflected on the reflectors 3 in order of the reflector 3Fc, the reflector 3Lc, the reflector 3Bc, the reflector 3Ic, the reflector 3Mc and the reflector 3Ec, and enters the side at which the emitting portion 20c is provided, as shown in FIG. 21. The ultraviolet ray that has entered the emitting portion 20c is reflected on the light source-side reflector and further emitted toward the reflector 3Ac.

That is, reflection of ultraviolet ray emitted from the emitting portion 20c continues repeatedly in order of the reflector 3Ac, the reflector 3Fc, the reflector 3Lc, the reflector 3Bc, the reflector 3Ic, the reflector 3Mc, the reflector 3Ec and the light source-side reflector, as shown in FIG. 21. As a result, in the cross-sectional direction of the one ultraviolet sterilizer 10c, ultraviolet ray emitted from the emitting portion 20c passes mainly through a center portion Ce inside the cylindrical casing 40c, and there are portions to which ultraviolet ray is not emit at a peripheral portion Pe. In FIG. 21, a passage region Fi1 that is a region through which ultraviolet ray emitted from the emitting portion 20c passes is indicated by a gray area. The passage region Fi1 corresponds to a screen-shaped sterilizing light screen based on ultraviolet ray.

As shown in FIG. 22, the centers of the two ultraviolet sterilizers 10c in the outflow direction agree with each other, and the positions of the emitting portions 20c of the two ultraviolet sterilizers 10c are different in the outflow direction. More specifically, in the ultraviolet sterilizer 100c, the emitting portion 20c of one of the ultraviolet sterilizers 10c is disposed in a state inclined by 45° relative to the emitting portion 20c of the other one of the ultraviolet sterilizers 10c. For this reason, ultraviolet ray is identified in all over the area in the ultraviolet sterilizer 100c. That is, ultraviolet ray is identified in any of the center portion Ce and the peripheral portion Pe.

Since ultraviolet ray of the two ultraviolet sterilizers 10c intensively passes through the center portion Ce inside the cylindrical casing 40c, the irradiance is higher than that of the peripheral portion Pe inside the cylindrical casing 40c. That is, in the air-conditioning apparatus 11c, the irradiance of ultraviolet ray in an overlap passage region Fi2 becomes relatively high. The overlap passage region Fi2 is a region in which the passage region Fi1 in one of the ultraviolet sterilizers 10c and the passage region Fit in the other one of the ultraviolet sterilizers 10c overlap. In FIG. 22, a difference in the irradiance of ultraviolet ray is expressed by thickening the gray color of the overlap passage region Fi2 that is the region in which the passage regions Fi1 overlap, as compared to the region in which the passage regions Fi1 do not overlap.

As described above, with the ultraviolet sterilizer 100c according to Embodiment 3, it is possible to emit ultraviolet ray all over the area in the cross section of the cylindrical casing 40c. The ultraviolet sterilizer 100c is able to provide a state where the irradiance of ultraviolet ray at the center portion inside the cylindrical casing 40c is large.

Incidentally, as shown in FIG. 23, the velocity of flow of air flowing through the casing 12 that is a cylindrical member, such as a duct having a radius of 100 mm, increases at the center portion of the casing 12 because of friction between air and the air course.

In this respect, with the ultraviolet sterilizer 100c according to Embodiment 3, even when the ultraviolet sterilizer 100c is mounted in the casing 12 in which the velocity of flow at the center portion increases, such as the inside of the duct, it is possible to gather ultraviolet ray at the center portion inside the cylindrical casing 40c. Therefore, as compared to the ultraviolet sterilizer 10a of Embodiment 1, it is possible to improve a sterilizing effect for microbes in the air.

In Embodiment 3, the ultraviolet sterilizer 100c in which the two ultraviolet sterilizers 10c each including the reflecting portion 30c of which the cross-sectional shape that is the front view when viewed from the inlet port 5 side in the axial longitudinal direction of the cylindrical casing 40c is a regular hexadecagonal cross-sectional shape are disposed is described; however, the ultraviolet sterilizer 100c is not limited to this. That is, as long as a structure reflects ultraviolet ray on reflectors such that ultraviolet ray gathers and crosses at the center portion inside the cylindrical casing 40c, the number of the ultraviolet sterilizers 10c, the number of the reflectors and the prism shape of the surface of each reflector may be selectively changed. At this time, to make the optical axes of rays of ultraviolet ray not parallel to each other, the positions of the emitting portions 20c in the outflow direction should be shifted. The air-conditioning apparatus 11c may be configured such that only one ultraviolet sterilizer 10c is mounted.

Embodiment 4

Figure 24:
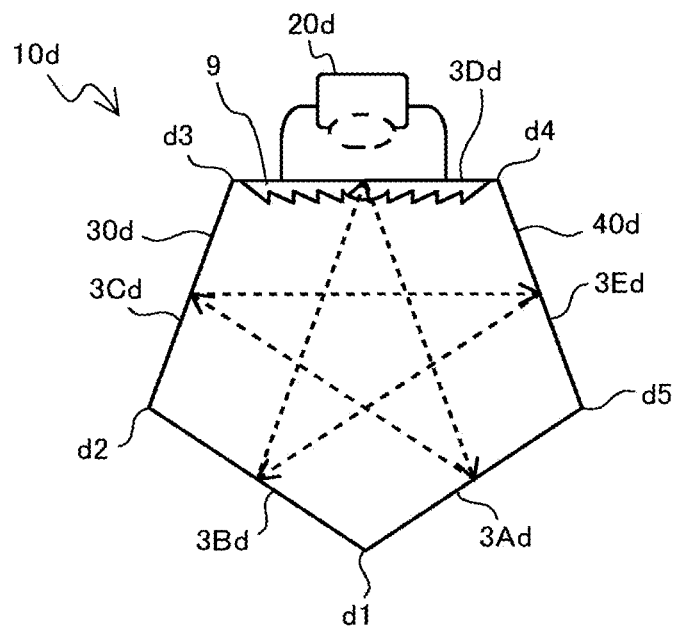
FIG. 24 is a schematic cross-sectional view that shows the configuration of an ultraviolet sterilizer according to Embodiment 4 of the present invention.

FIG. 24 is a schematic cross-sectional view that shows the configuration of an ultraviolet sterilizer according to Embodiment 4 of the present invention. As shown in FIG. 24, in the ultraviolet sterilizer 10d according to Embodiment 4, the cross-sectional shape that is a front view from the inlet port 5 side in the axial longitudinal direction of a cylindrical casing 40d is a regular pentagonal shape, and all the surface shapes of the reflectors 3 are worked into a flat shape. The ultraviolet sterilizer 10d has a Fresnel lens 9 at a side at which an emitting portion 20d is disposed among the sides of the regular pentagonal shape that is the cross-sectional shape. Excepting the above point, the ultraviolet sterilizer 10d is configured as in the case of the ultraviolet sterilizer 10a of the above-described Embodiment 1. The emitting portion 20d is configured as in the case of the emitting portion 20a of Embodiment 1. Thus, like reference numerals denote equivalent constituent members to those of the above-described Embodiment 1, and the description is omitted.

As shown in FIG. 24, the cross-sectional shape of the ultraviolet sterilizer 10d, that is, the front view when viewed from the inlet port 5 side in the axial longitudinal direction of the cylindrical casing 40d, is a regular pentagonal shape. That is, the ultraviolet sterilizer 10d includes the cylindrical casing 40d, the emitting portion 20d and the reflecting portion 30d. The cross-sectional shape of the cylindrical casing 40d is a regular pentagonal shape. The emitting portion 20d is disposed at the outer peripheral portion of the cylindrical casing 40d. The reflecting portion 30d is arranged on the inner surface of the cylindrical casing 40d, and the cross-sectional shape of the reflecting portion 30d is a regular pentagonal annular shape. In the ultraviolet sterilizer 10d, the Fresnel lens 9 is disposed in front of an ultraviolet ray emitting element.

The reflecting portion 30d includes a plurality of reflectors 3Ad to 3Ed that reflect ultraviolet ray. The reflectors 3Ad to 3Ed respectively constitute the sides of the regular pentagonal shape that is the cross-sectional shape of the reflecting portion 30d. Hereinafter, the reflectors 3Ad to 3Ed are also simply collectively referred to as the reflectors 3 or any one of the reflectors 3Ad to 3Ed is also simply referred to as the reflector 3.

Figure 25:
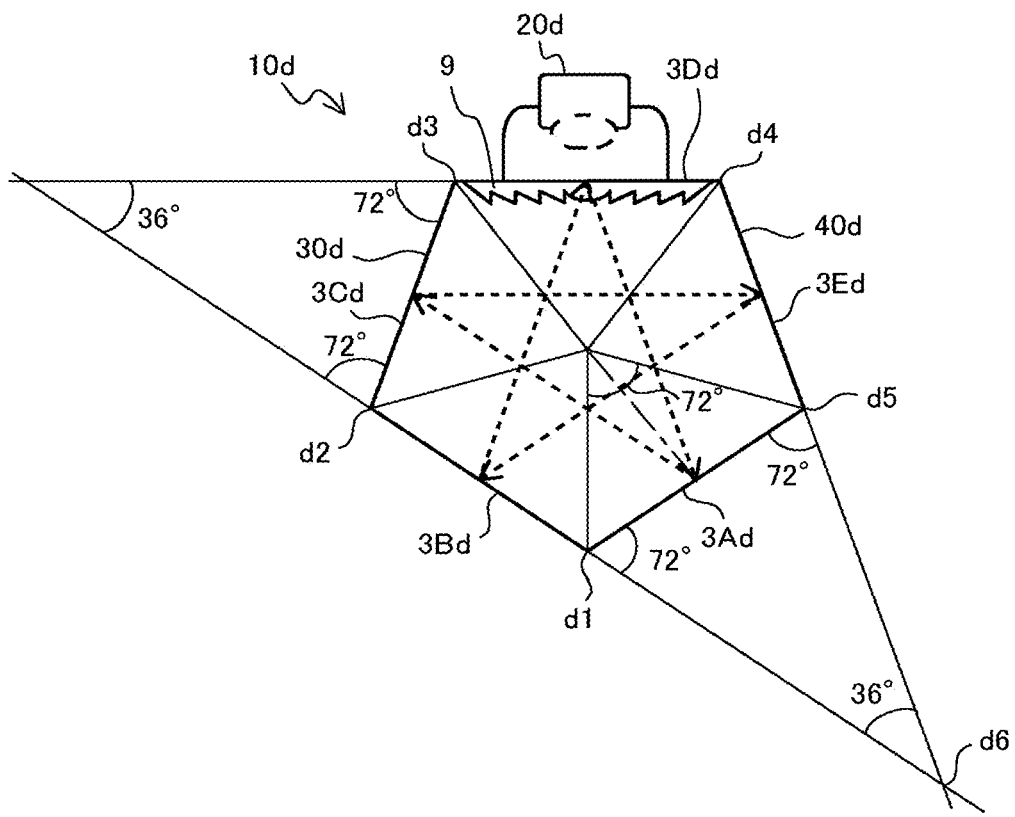
FIG. 25 is a diagram that shows a path along which ultraviolet ray travels in a reflecting portion shown in FIG. 24.

FIG. 25 is a diagram that shows a path through which ultraviolet ray travels in the reflecting portion 30d shown in FIG. 24. The traveling direction of ultraviolet ray emitted from the emitting portion 20d in the cross section direction of the cylindrical casing 40d will be described with reference to FIG. 25. The ultraviolet sterilizer 10d is configured such that ultraviolet ray that is emitted from the emitting portion 20d enters the facing reflector 3Ad at an angle of 72°.

As shown in FIG. 25, the five vertices of the regular polygonal shape that is the cross-sectional shape of the ultraviolet sterilizer 10d are respectively a vertex d1, a vertex d2, a vertex d3, a vertex d4 and a vertex d5, and the reflectors 3 are the reflector 3Ad, the reflector 3Bd, the reflector 3Cd, the reflector 3Dd and the reflector 3Ed in the clockwise direction in order from the reflector 3 located at the side on the right side of the vertex d1.

In the regular pentagonal shape that is the cross-sectional shape of the ultraviolet sterilizer 10d, all the central angles are 72°, so a triangle connecting the intersection of extension lines of the sides across one side to the intersection-side vertices of those sides is an isosceles triangle having an apex angle of 36°. That is, for example, when it is assumed that the sides across one side are the side at which the reflector 3Bd is located and the side at which the reflector 3Ed is located, and the intersection of the extension lines of these sides is an intersection d6 as shown in FIG. 25, a triangle that connects the vertex d1, the intersection d6 and the vertex d5 is an isosceles triangle having two angles of 72°. For this reason, when ultraviolet ray is caused to enter the reflector 3Ad at an angle of 72°, the ultraviolet ray is reflected at a reflection angle of 18°, and the reflected ultraviolet ray enters the reflector 3Cd at an incident angle of 72°. As shown in FIG. 25, the ultraviolet ray reflected on the reflector 3Cd is reflected on the reflectors 3 along the radial direction of the cylindrical casing 40d in order of the reflector 3Ed, the reflector 3Bd, the reflector 3Dd, the reflector 3Ad and the reflector 3Cd. That is, ultraviolet ray emitted from the emitting portion 20d is sequentially repeatedly reflected along the radial direction of the cylindrical casing 40d on the five reflectors 3, so the ultraviolet ray is reflected all over the area in the cross section of the cylindrical casing 40d, as shown in FIG. 25.

As described above, with the ultraviolet sterilizer 10d, even when the surface of each reflector 3 is not worked into a prism shape, it is possible to emit ultraviolet ray all over the area in the cross section of the cylindrical casing 40d by utilizing the plurality of reflectors 3 of which the surface is a flat shape. That is, in Embodiment 4, since no special working needs to be applied to each reflector 3, it is possible to easily prepare the ultraviolet sterilizer 10d.

Figures 26, 27:
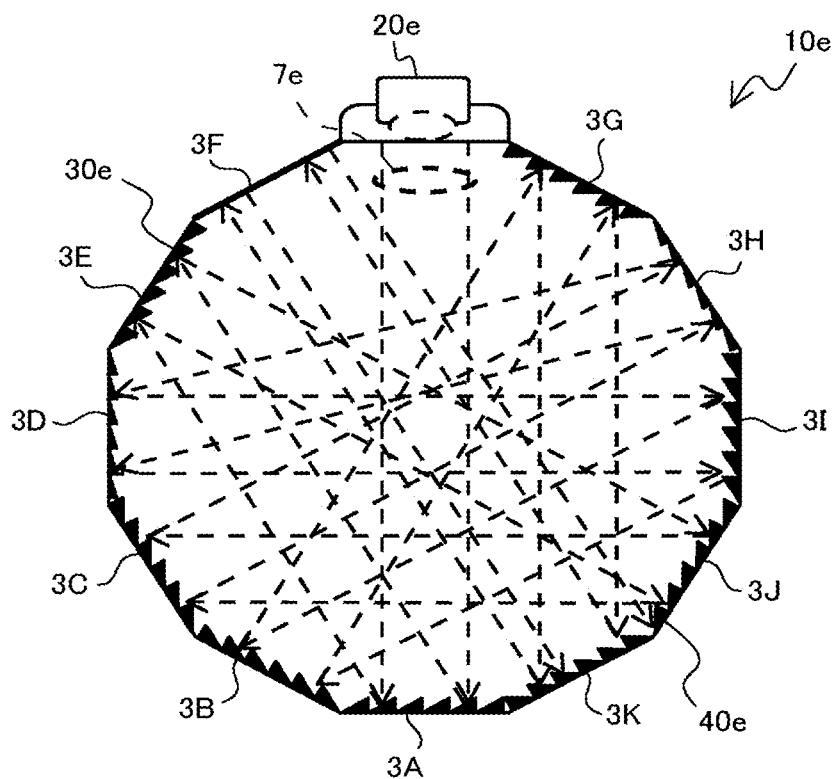
FIG. 26 is a table that shows an ultraviolet ray irradiance at the level of 1 mm above each reflector shown in FIG. 24.
FIG. 27 is a schematic cross-sectional view that shows the configuration of an ultraviolet sterilizer according to Embodiment 5 of the present invention.

FIG. 26 is a table that shows an ultraviolet ray irradiance at the level of 1 mm above each reflector 3 shown in FIG. 24. An increase in ultraviolet ray irradiance due to reflection at each reflector 3 will be specifically described with reference to FIG. 26.

In Embodiment 4 as well, an ultraviolet ray irradiance provided by the ultraviolet sterilizer 10d is defined as expressed by the mathematical expression 1. An ultraviolet intensity is a quantity obtained by accumulating the intensity of ultraviolet ray that enters each reflector 3 and the intensity of ultraviolet ray that has been reflected on each of the reflectors 3 in the case where ultraviolet ray emitted from the emitting portion 20d has been reflected until the total radiant flux of ultraviolet ray attenuates to 1%. For example, when the emitting portion 20d emits parallel rays at 0.01 W/cm$^2$ and the area of the emitting portion 20d is 75 cm$^2$ (10 cm×7.5 cm), the total radiant flux of ultraviolet ray is 0.75 W. When the thickness of the ultraviolet sterilizer 10d in an air course direction is 1 cm, an air velocity caused by the air-sending device 15 is 3 m/s, so an irradiation time is 0.0033 s.

Since ultraviolet ray emitted from the emitting portion 20d continues to be reflected on the reflectors 3 until the total radiant flux attenuates to 1% or below, the ultraviolet ray irradiance on each reflector 3 becomes about 2.65 mW·s/cm$^2$. At the portion at which ultraviolet ray from each reflector 3 to a corresponding one of the reflectors 3 overlaps each other, including the center portion of the ultraviolet sterilizer 10d, an accumulated value of the irradiances of the overlapping rays of ultraviolet ray is an ultraviolet ray irradiance, so the ultraviolet ray irradiance further increases.

As described above, the ultraviolet sterilizer 10d is able to increase the ultraviolet ray irradiance to 2.0 mW·s/cm$^2$ or above all over the cross section.

As described above, when ultraviolet ray having a wavelength of 254 nm is emit to airborne influenza virus at 2 mW·s/cm$^2$, it is possible to deactivate the airborne influenza virus by 99%. In this respect, the ultraviolet sterilizer 10d is able to increase the ultraviolet ray irradiance to 2 mW·s/cm$^2$ or above, at which airborne influenza virus is able to be deactivated by 99%, over all the area in the cross section within the ultraviolet sterilizer 10a with the use of ultraviolet ray emitted from the emitting portion 20d.

In the ultraviolet sterilizer 10d, variations in ultraviolet ray irradiance on the reflectors 3 are reduced to 15.5% relative to the average value of the ultraviolet ray irradiances. This will be described below. In the case of Embodiment 4, different from Embodiment 1, as shown in FIG. 26, ultraviolet ray emitted from the emitting portion 20d is reflected in order of the reflector 3Ad, the reflector 3Cd, the reflector 3Ed, the reflector 3Bd and the reflector 3Dd, and is further reflected on the reflectors 3 along the radial direction of the cylindrical casing 40d in order of the reflector 3Ad, the reflector 3Cd, the reflector 3Ed, the reflector 3Bd and the reflector 3Dd. That is, ultraviolet ray emitted from the emitting portion 20d are sequentially repeatedly reflected on the five reflectors 3 along the radial direction of the cylindrical casing 40d. As a result, in the ultraviolet sterilizer 10d, the numbers of reflections of ultraviolet ray on the reflectors 3 are equivalent to one another, so it is possible to reduce variations in ultraviolet ray irradiance on the reflectors 3. That is, the ultraviolet sterilizer 10d is able to suppress variations in ultraviolet ray irradiance on the reflectors 3 to about 15% relative to the average value, so it is possible to increase the uniformity of the ultraviolet ray irradiance.

[Ultraviolet Light Source]

The emitting portion 20d that is the ultraviolet ray source will be described.

The emitting portion 20d is configured to cause ultraviolet ray to enter the facing reflector 3 at an angle of 72°. In Embodiment 4, the emitting portion 20d has a structure such that the Fresnel lens 9 is disposed in front of the ultraviolet ray emitting element. The Fresnel lens 9 is a lens such that a normal lens is divided into concentric regions and the thickness of each divided region is reduced. The Fresnel lens 9 has a sawtooth cross section. The Fresnel lens 9 has the function of emitting ultraviolet ray that has entered from the ultraviolet ray emitting element, in a certain specific direction in form of parallel rays.

As long as ultraviolet ray that has entered from the ultraviolet ray emitting element is able to be emitted in a certain specific direction in form of parallel rays, the emitting portion 20d may include another lens, or the like, other than the Fresnel lens 9. The emitting portion 20d may be formed of a light emitter that also has a similar function to the function of the Fresnel lens 9. In addition, the emitting portion 20d may be configured such that the ultraviolet ray emitter including the ultraviolet ray emitting element and the collimate lens is disposed vertically relative to a direction in which ultraviolet ray is intended to be emitted, and parallel rays of ultraviolet ray may be caused to enter the facing reflector 3 at an angle of 72°. A reflector may be provided behind the ultraviolet ray emitter, and parallel rays of ultraviolet ray may be caused to enter the facing reflector 3 at an angle of 72°.

[Method of Preparing Reflectors]

A method of preparing the reflectors 3 will be described.

An ultraviolet ray reflecting material as in the case of the above-described Embodiment 1 may be used as the material of each reflector 3. When a surface treatment, such as an electroplating method and a vapor deposition method, is applied to the ultraviolet ray reflecting material, the surface has a high reflectance. In addition, because of the reason why workability is excellent, using aluminum as the ultraviolet ray reflecting material is particularly desirable.

Next, a method of molding each reflector 3 will be described.

Initially, a metal flat plate is cut into a length approximately equal to the thickness d of the cylindrical casing 40d in the air flow direction Da. After that, the cut metal flat pate is bent into a regular pentagonal shape by mechanical bending, such as hand bending, pressing, roll bender and roll forming.

Each reflector 3 may be prepared as follows as in the case of Embodiment 1. A base having the same shape as the reflector 3 is molded by using a material other than a metal, such as a resin material, and then metal powder paste is evaporated onto the surface of the material. With this configuration, it is possible to reduce cost and to increase the easiness of molding.

In Embodiment 4, the ultraviolet sterilizer 10d of which the cross-sectional shape that is the front view when viewed from the inlet port 5 side in the axial longitudinal direction of the cylindrical casing 40d is a regular pentagonal shape is illustrated and described; however, the ultraviolet sterilizer 10d is not limited to this. That is, the ultraviolet sterilizer 10d may, for example, have a cross-sectional shape that is a regular polyhedral shape having odd vertices, such as a regular heptagonal shape and a regular nonagonal shape. With the thus configured ultraviolet sterilizer 10d, even when the surface of each reflector 3 is not worked into a prism shape, it is possible to emit ultraviolet ray all over the area in the cross section of the cylindrical casing 40d by utilizing the plurality of reflectors 3 of which the surface has a flat shape.

In Embodiment 4, the case where the single ultraviolet sterilizer 10d is installed in the air-conditioning apparatus 11a is described; however, the configuration is not limited to this. Two or more ultraviolet sterilizers 10d may be mounted on the air-conditioning apparatus 11a. With this configuration, it is possible to increase the ultraviolet ray irradiance and the irradiation direction of ultraviolet ray in the cross section perpendicular to the air flow direction Da, so it is possible to further increase a sterilizing effect.

Embodiment 5

Figure 28:
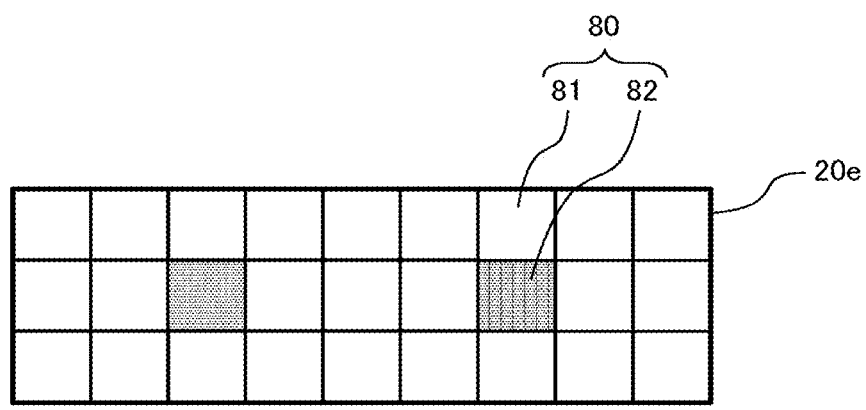
FIG. 28 is a schematic cross-sectional view of an emitting portion of the ultraviolet sterilizer shown in FIG. 27.

FIG. 27 is a schematic cross-sectional view that shows the configuration of an ultraviolet sterilizer according to Embodiment 5 of the present invention. FIG. 28 is a schematic cross-sectional view of an emitting portion of the ultraviolet sterilizer shown in FIG. 27. The ultraviolet sterilizer 10e according to Embodiment 5 includes the emitting portion 20e that serves as an ultraviolet ray source, as shown in FIG. 27, and the emitting portion 20e includes a plurality of light emitting elements 80. In the emitting portion 20e, as shown in FIG. 28, a plurality of ultraviolet ray emitting elements 81 and at least one visible light emitting element 82 are disposed as the plurality of light emitting elements 80. The ultraviolet ray emitting elements 81 each are formed of, for example, a UV-LED and emit ultraviolet ray. The at least one visible light emitting element 82 is formed of, for example, a visible light-LED and emits visible light. That is, the broken line arrows 7e in FIG. 27 illustrate the fluxes of ultraviolet ray and visible light that are emitted from the emitting portion 20e and reflected on the reflectors 3 and also illustrate the traveling directions of the fluxes of ultraviolet ray and visible light. Excepting the above point, the ultraviolet sterilizer 10e is configured similarly to the ultraviolet sterilizer 10a of the above-described Embodiment 1. Thus, like reference numerals denote equivalent constituent members to those of the ultraviolet sterilizer 10a in Embodiment 1, and the description is omitted.

[Visible Light Source]

Visible light that the visible light emitting element 82 emits may be any visually recognizable light. That is, light having a wavelength of 360 nm to 830 nm may be used as visible light that the emitting portion 20e emits. Desirably, the emitting portion 20e should be configured to emit visible light having a wavelength of 400 nm to 760 nm, which is visually recognizable by almost all the humans.

[Visible Light Emitting Element]

Subsequently, the visible light emitting element 82 of the emitting portion 20e will be described.

To make it possible to keep track of ultraviolet ray that is emitted from the ultraviolet ray emitting elements 81 visually, the visible light emitting element 82 is disposed such that visible light that is emitted from the visible light emitting element 82 passes through a similar path to the path through which ultraviolet ray that is emitted from the ultraviolet ray emitting elements 81 passes.

The ultraviolet ray source of the emitting portion 20e has a structure configured to emit parallel rays having strong directivity in addition to the ultraviolet ray emitting elements 81. For this reason, a visible light source that is disposed in the emitting portion 20e also has a similar structure configured to emit parallel rays having strong directivity to the ultraviolet ray source of the emitting portion 20e.

In Embodiment 5, the structure that the collimate lens is disposed inside the visible light emitting element 82 is employed; however, the structure is not limited to this. Instead of the collimate lens, for example, a Fresnel lens may be provided. A reflector may be provided behind the light source.

The visible light emitting element 82, the collimate lens, and other components, may be packaged or modularized as a visible light source. By packaging or modularizing the visible light emitting element 82, the collimate lens, and other components, simple installation of the emitting portion 20e is possible.

The emitting portion 20e emits parallel rays of ultraviolet ray from the entire surface defined by the sides along the air flow direction Da and one of the sides of the regular dodecagonal shape that is the cross-sectional shape, in the reflecting portion 30e at which the emitting portion 20e is installed. For this reason, one or two of the visible light emitting elements 82 are disposed at the center of the emitting portion 20e such that visible light travels at the center portion of an ultraviolet ray plane that is emitted from the emitting portion 20e. FIG. 28 illustrates the case where the emitting portion 20e has the two visible light emitting elements 82; however, the configuration is not limited to this. The emitting portion 20e may have the single visible light emitting element 82 at the center. FIG. 28 illustrates the case where the ultraviolet ray emitting elements 81 are disposed between one of the visible light emitting elements 82 and the other one of the visible light emitting elements 82; however, the configuration is not limited to this. The two visible light emitting elements 82 may be arranged next to each other.

[Method of Preparing Reflectors]

Next, a method of preparing the reflectors 3 of which the surface has a prism shape will be described.

Since the shape of each of the reflectors 3 that constitute the reflecting portion 30e is similar to that in the case of the above-described Embodiment 1, the prism shape of each reflector 3 will be initially described with reference to FIG. 4. The average pitch Ap that is the length of the flat surface of each right-angled triangle in the prism shape shown in FIG. 4 should be 0.01 mm to 10 mm, and desirably should be 0.1 mm to 10 mm.

Subsequently, the base material of each reflector 3 will be described.

The usable reflecting material is desirably a material that is able to reflect ultraviolet ray and visible light at a reflectance of 40% or above, desirably 60% or above and more desirably 70% or above. Examples of the usable reflecting material include magnesium carbonate (visible light reflectance: about 90% or above, ultraviolet ray reflectance: about 75%) and calcium carbonate (visible light reflectance: about 90% or above, ultraviolet ray reflectance: about 75%). In addition, the desirable reflecting material to be used is a material that is able to reflect visible light at the same level as an ultraviolet ray reflectance. Examples of the ultraviolet ray reflecting material that is suitably usable in the ultraviolet sterilizer 10e include platinum (ultraviolet ray reflectance and visible light reflectance: about 50%), aluminum (ultraviolet ray reflectance and visible light reflectance: about 90%) and magnesium oxide (ultraviolet ray reflectance and visible light reflectance: about 90% to 99%). Additionally, when a surface treatment, such as an electroplating method and a vapor deposition method, is applied to these ultraviolet ray reflecting materials, the surface has a high reflectance.

Since aluminum is excellent in workability, aluminum may be suitably used as the ultraviolet ray reflecting material and the visible light reflecting material. By further coating aluminum with magnesium fluoride $MgF_2$ as a surface treatment for aluminum, it is possible to protect the surface of the aluminum material and increase the reflectance in the ultraviolet range.

Subsequently, a method of molding the single reflector 3 of which the surface has a prism shape will be described.

Initially, a method of preparing the single reflector 3 shown in FIG. 4 will be described. First, a die for the single reflector 3 is prepared. A material plate for the reflector 3, cut into a length approximately equal to the thickness d of the cylindrical casing 40a in the air flow direction Da is put on the prepared die, and the put material plate is worked by mechanical bending, such as hand bending, pressing, roll bender and roll forming.

The reflector 3 may be formed by cutting and working a metal plate having a thickness larger than an average depth. Alternatively, the single reflector 3 may be prepared as follows. A base having the same shape as the single reflector 3 is molded by using a material other than the above-described metal, and then metal powder paste is evaporated onto the surface of the base. In this case, a die having the shape of the single reflector 3 is prepared, and a member that corresponds to the base may be formed by using a resin material by press working, injection molding, compression molding, or the like. After that, metal powder paste that becomes a reflecting material is evaporated onto the surface layer of the base, thus forming the reflector 3. In this way, when the reflector 3 is formed by using a combination of a resin material and evaporation of metal powder paste, it is advantageous in that material cost is reduced as compared to when a metal plate is used and this combination is easier to be molded than the metal material.

A thermoplastic resin, such as polyethylene (PE), polypropylene (PP), polyvinyl chloride (PVC), polyethylene terephthalate (PET) and ABS resin, may be used as a resin material for molding a base. The base of each reflector 3 may be molded by using a thermosetting resin, such as phenolic resin, amino resin, epoxy resin and urethane resin, synthetic rubber, such as polyisoprene and butadiene, and synthetic fiber, such as nylon, vinylon, acrylic fiber and rayon, that are plastic materials other than the above.

Next, a method of assembling the reflecting portion 30e by mating the single reflectors 3 will be described. Initially, an assembly jig that is utilized at the time of assembling the reflecting portion 30e by mating the single reflectors 3 is prepared. The assembly jig is an apparatus for directing or guiding working positions of parts and tools. Subsequently, the reflectors 3 and the emitting portion 20e are set in the assembly jig. After that, visible light is emitted from the emitting portion 20e. Each reflecting surface is minutely adjusted while the visible light is kept track of. The surfaces of the reflecting portion 30e are adjusted and assembled such that visible light is reflected on all the reflecting surfaces. The reflecting portion 30e is provided inside the cylindrical casing 40e.

As described above, the ultraviolet sterilizer 10e allows the optical path of UV light to be visually recognized with visible light at the time of manufacturing the reflecting portion 30e, so it is possible to easily assemble and prepare the ultraviolet sterilizer 10e. The ultraviolet sterilizer 10e also allows the optical path of UV light to be visually recognized with visible light at the time of ultraviolet sterilization, so a user, or the like, is allowed to visually recognize whether sterilization is being properly performed by UV light. In addition, when at least one of the ultraviolet ray emitting elements 81 is short circuited at the time of ultraviolet sterilization, the ultraviolet sterilizer 10e is configured such that the visible light emitting element 82 does not turn on. For this reason, with the ultraviolet sterilizer 10e, it is possible to find a short circuit in the ultraviolet ray emitting elements 81 by making sure that visible light is not turned on, so it is possible to visually check the service life of the ultraviolet ray emitting elements 81.

Embodiment 6

Figure 29:
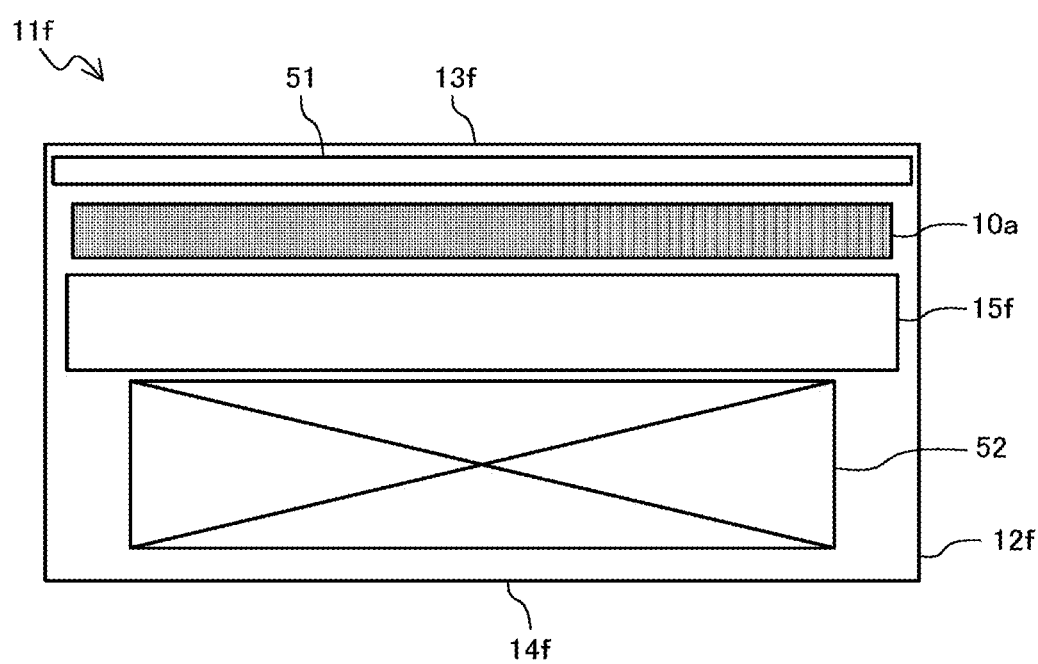
FIG. 29 is a schematic diagram that illustrates the schematic configuration of an air-conditioning apparatus according to Embodiment 6 of the present invention.

FIG. 29 is a schematic diagram that illustrates the schematic configuration of an air-conditioning apparatus according to Embodiment 6. The air-conditioning apparatus 11f on which the ultraviolet sterilizer 10a described in Embodiment 1 is mounted inside will be described with reference to FIG. 29. Like reference numerals denote equivalent constituent members to those of the above-described Embodiment 1, and the description is omitted.

As shown in FIG. 29, the air-conditioning apparatus 11f in Embodiment 6 includes a casing 12f. The casing 12f includes an air intake 13f and an outlet opening 14f. The air intake 13f introduces air. Through the outlet opening 14f air introduced from the air intake 13f flows out. The air-conditioning apparatus 11f further includes a prefilter 51, an air-sending device 15f and a heat exchanger 52. The prefilter 51 removes dust and trash contained in air introduced from the air intake 13f into the casing 12f. The air-sending device 15f generates flow of air from the air intake 13 toward the outlet opening 14. The heat exchanger 52 is formed of, for example, a fin and tube heat exchanger. The air-conditioning apparatus 11f includes the ultraviolet sterilizer 10a installed at the air inlet side of the air-sending device 15f. That is, in the air-conditioning apparatus 11f, air introduced from the air intake 13f flows out from the outlet opening 14f through the prefilter 51, the ultraviolet sterilizer 10a, the air-sending device 15f and the heat exchanger 52.

Inside the air-conditioning apparatus 11f, air pumped by the air-sending device 15f and introduced from the air intake 13f definitely passes through the blade portion of the air-sending device 15f. For this reason, in the air-conditioning apparatus 11f, the ultraviolet sterilizer 10a is disposed such that the ultraviolet sterilizer 10a covers the blade portion of the air-sending device 15f. As the air-conditioning apparatus 11f starts operating, the air-sending device 15f works, and air flows from an interior, or other space, into the casing 12f. The ultraviolet sterilizer 10a sterilizes microbes in the air flowing into the casing 12f.

In this way, the air-conditioning apparatus 11f in which the ultraviolet sterilizer 10a is installed is able to sterilize microbes, such as fungi, bacteria and viruses, in the air introduced into the casing 12f. For this reason, with the air-conditioning apparatus 11f, it is possible to inhibit adhesion of microbes to the inside of the air-conditioning apparatus 11f and proliferation of the microbes, so it is possible to reduce the number of microbes in the air in an interior, or other space. By inhibiting adhesion of microbes to the inside of the air-conditioning apparatus 11f and proliferation of microbes inside the air-conditioning apparatus 11f, it is possible to reduce odor that is generated from the air-conditioning apparatus 11f.

In Embodiment 6, a structure that the air-conditioning apparatus 11f takes air in from the air intake 13f and air from the outlet opening 14f flows out through the prefilter 51, the air-conditioning apparatus 11f, the air-sending device 15f and the heat exchanger 52 is described; however, the structure is not limited to this. That is, even when the air-conditioning apparatus 11f has another configuration that the air-sending device 15f is disposed, for example, downstream of the heat exchanger 52, similar advantageous effects are expected when the ultraviolet sterilizer 10a is disposed at a location through which air taken into the casing 12f passes. From the viewpoint of inhibiting adhesion of microbes to the constituent members inside the air-conditioning apparatus 11f, the configuration that the ultraviolet sterilizer 10a is disposed upstream of the air-sending device 15f and the heat exchanger 52 is desirable.

Embodiment 7

In Embodiment 7, mounting the ultraviolet sterilizer 10a on an air cleaner will be described. The air cleaner in Embodiment 7 has the same components as the air-conditioning apparatus 11f of Embodiment 6, so like reference numerals are used, and the description is omitted. As the air cleaner starts operating, an air-sending device works, and air flows from an interior, or other space, into the casing 12f. The ultraviolet sterilizer 10a sterilizes microbes in the air flowing into the casing 12f.

In this way, the air cleaner in which the ultraviolet sterilizer 10a is installed is able to sterilize microbes, such as fungi, bacteria and viruses, in the air taken into the casing 12f. For this reason, with the air cleaner, it is possible to inhibit adhesion of microbes to the inside of the air cleaner and proliferation of the microbes, so it is possible to reduce the number of microbes in the air in an interior, or other space. By inhibiting adhesion of microbes to the inside of the air cleaner and proliferation of microbes inside the air cleaner, it is possible to reduce odor that is generated from the air cleaner.

The above-described Embodiments are suitable specific examples of the ultraviolet sterilizer and the air-conditioning apparatus, including the air cleaner, and the technical scope of the invention is not limited to these modes. For example, in the above-described Embodiments, description is made on the assumption that the thickness d of each of the ultraviolet sterilizers 10a, 10c, 10d, 10e in the air flow direction Da, that is, the thickness of the screen-shaped sterilizing light screen based on ultraviolet ray that is generated by each of the ultraviolet sterilizers 10a, 10c, 10d, 10e is 1 cm or 10 cm; however, the configuration is not limited to this. For example, when the thickness d is increased, an ultraviolet ray irradiation time extends, so a sterilizing effect increases. On the other hand, when the thickness d is reduced, a compact design is possible, so it is advantageous in that it is allowed to be mounted inside a relatively small-sized device.

The cross-sectional shape of the ultraviolet sterilizer of the invention, that is, the front view when viewed from the inlet port 5 side in the axial longitudinal direction of the cylindrical casing 40a, is not limited to a regular pentagonal shape, a regular dodecagonal shape or a regular hexadecagonal shape, and may be various polygonal shapes. That is, the cross-sectional shape of the reflecting portion is formed into a selected polygonal annular shape. The inclination angle α of each of the reflectors should be adjusted based on the principles of the incident angle and reflection angle of light, or the like. When the number of the sides of a polygonal shape increases, the shape of a reflecting portion approaches to a circular shape. Therefore, when the ultraviolet sterilizer is disposed at a circular portion, such as a duct, of the air-conditioning apparatus, it is possible to further reduce an increase in pressure loss.

In addition, two or more of the ultraviolet sterilizers 10a, 10c, 10d, 10e described in the above Embodiments may be mounted on a device, such as the air-conditioning apparatus, in combination. At this time, the positions of the emitting portions of the ultraviolet sterilizers should be shifted such that the optical axes of rays of ultraviolet ray in the ultraviolet sterilizers are not parallel to each other.

Furthermore, in the above-described Embodiments, description is made on the assumption that the ultraviolet sterilizer is mounted on the air-conditioning apparatus; however, the configuration is not limited to this. The ultraviolet sterilizer of the present invention is also allowed to be mounted on a device other than the air-conditioning apparatus. That is, the ultraviolet sterilizer may be configured to set not only air but also various fluids including liquid as a sterilizing target.

In the above-described Embodiments, the case where the diameter of the circular shape of the casing 12 is 100 mm is illustrated; however, the case is not limited to this. The diameter of the circular shape of the casing 12 should be changed as needed in response to, for example, application of a device on which the casing 12 is mounted.

REFERENCE SIGNS LIST 3, 3A to 3K, 3Ac to 3Oc, 3Ad to 3Ed reflector 5 inlet port 6 outlet port 7, 7e broken line arrow 9 Fresnel lens 10a to 10e, 100c ultraviolet sterilizer 11a to 11c, 11e, 110a air-conditioning apparatus 12, 12f casing 13, 13f air intake 14, 14f outlet opening 15, 15f air-sending device 20a, 20c, 20d, 20e emitting portion 30a, 30c, 30d, 30e reflecting portion 31 flat part 31a flat surface 32 reflecting part 32a reflecting surface 40a, 40c, 40d, 40e cylindrical casing 51 prefilter 52 heat exchanger 71 incident light 72 reflected light 73 normal 80 light emitting element 81 ultraviolet ray emitting element 82 visible light emitting element d thickness α inclination angle

The invention claimed is:

1. An air-conditioning apparatus configured to condition introduced air, the air-conditioning apparatus comprising:
a cylindrical casing including an inlet port through which air flows in and an outlet port through which the air flows out, the air passing through the cylindrical casing;
an ultraviolet sterilizer configured to emit parallel ultraviolet rays to the air, the ultraviolet sterilizer including a sterilizing light screen forming unit configured to form a screen-shaped sterilizing light screen formed by the emitted parallel ultraviolet rays crossing with itself and emitted in a direction along a radial direction of the casing, the sterilizing light screen crossing an outflow direction from the inlet port to the outlet port; and
a reflecting portion, whose cross-sectional shape is polygonal, configured to reflect the emitted parallel ultraviolet rays multiple times along the radial direction of the casing on a plane perpendicular to the outflow direction,
wherein the reflecting portion includes a plurality of groups of reflectors that reflect the ultraviolet ray, the plurality of groups of reflectors are positioned adjacent each other along an inner circumferential surface of the cylindrical casing,
wherein each group of reflectors includes a plurality of reflectors each having a reflecting surface that reflects the ultraviolet ray,
wherein each projecting surface of the plurality of reflectors in a respective group of reflectors, projects inwardly from the inner circumferential surface at a same angle relative to the inner circumferential surface,
wherein an orientation of the angle of the reflectors in each group changes between a respective group of reflectors and an adjacent group of reflectors along the inner circumferential surface,
wherein the same angle within each of the group of reflectors is one of an upwardly sloping angle or a downwardly sloping angle, and
wherein the sloping angle of the reflectors point both towards each other and away from each other in respective adjacent groups of reflectors of the plurality of groups of reflectors along the inner circumferential surface.

2. The air-conditioning apparatus of claim 1, wherein the sterilizing light screen forming unit includes an emitting portion configured to emit the parallel rays as the ultraviolet ray along the radial direction of the casing.

3. The air-conditioning apparatus of claim 1, wherein a front view of the reflecting portion when viewed from a side of the inlet port in an axial longitudinal direction of the casing is a polygonal annular shape.

4. The air-conditioning apparatus of claim 3, wherein the reflectors are disposed in the polygonal annular shape in the front view.

5. The air-conditioning apparatus of claim 4, wherein each of the reflectors includes a flat part extending along an inner surface of the casing.

6. The air-conditioning apparatus of claim 4, wherein each of the reflectors has a prism-shaped surface.

7. The air-conditioning apparatus of claim 3, wherein the ultraviolet ray that the reflecting portion has reflected multiple times crosses with itself at a central part of the sterilizing light screen.

8. The air-conditioning apparatus of claim 3, wherein the emitting portion includes
an ultraviolet ray emitter configured to emit the ultraviolet ray, and
a light source-side reflector disposed on an outer side of the ultraviolet ray emitter in the radial direction of the casing, wherein the light source-side reflector is configured to reflect the ultraviolet ray, emitted from the ultraviolet ray emitter, to an inner side in the radial direction of the casing.

9. The air-conditioning apparatus of claim 8, wherein the ultraviolet ray emitter includes
a plurality of ultraviolet ray emitting elements configured to emit the ultraviolet ray, and
the emitting portion includes at least one visible light emitting element configured to emit visible light.

10. The air-conditioning apparatus of claim 3, wherein the emitting portion includes
a plurality of ultraviolet ray emitting elements that emit the ultraviolet ray, and
at least one visible light emitting element configured to emit visible light.

11. The air-conditioning apparatus of claim 1, further comprising
an air-conditioning apparatus casing having an air intake configured to introduce the air and an outlet opening through which the air introduced from the air intake flows out,
wherein a flow direction from the air intake toward the outlet opening agrees with the outflow direction.

12. The air-conditioning apparatus of claim 11, wherein an inside diameter of the inlet port is larger than or equal to an inside diameter of the air intake, and
an inside diameter of the outlet port is larger than or equal to an inside diameter of the outlet opening.

13. An ultraviolet sterilizer that sterilizes air with parallel ultraviolet rays, the ultraviolet sterilizer comprising:

a cylindrical casing including an inlet port through which the air flows in and an outlet port through which the air flows out, the air passing through the casing;

a sterilizing light screen forming unit configured to form a screen-shaped sterilizing light screen formed by the emitted parallel ultraviolet rays crossing with itself by emitting the ultraviolet ray in a direction along a radial direction of the casing, the light screen crossing an outflow direction from the inlet port to the outlet port; and a reflecting portion, whose cross-sectional shape is polygonal, configured to reflect the emitted parallel ultraviolet rays multiple times along the radial direction of the casing on a plane perpendicular to the outflow direction, wherein the reflecting portion includes a plurality of groups of reflectors that reflect the ultraviolet ray, the plurality of groups of reflectors are positioned adjacent each other along an inner circumferential surface of the cylindrical casing, wherein each group of reflectors includes a plurality of reflectors each having a reflecting surface that reflects the ultraviolet ray projects inwardly from the inner circumferential surface at a same angle relative to the inner circumferential surface, wherein an orientation of the angle of the reflectors in each group changes between a respective group of reflectors and an adjacent group of reflectors along the inner circumferential surface, wherein the same angle within each of the group of reflectors is one of an upwardly sloping angle or a downwardly sloping angle, and wherein the sloping angle of the reflectors point both towards each other and away from each other in respective adjacent groups of reflectors of the plurality of groups of reflectors along the inner circumferential surface.

14. The ultraviolet sterilizer of claim 13, wherein the sterilizing light screen forming unit includes an emitting portion that emits the parallel rays as the ultraviolet rays along the radial direction of the cylindrical casing.

15. The ultraviolet sterilizer of claim 14, wherein
the emitting portion includes
a plurality of ultraviolet ray emitting elements that emit the ultraviolet ray, and
at least one visible light emitting element configured to emit visible light.

16. The air-conditioning apparatus of claim 1, wherein
the emitting portion has a rear end in the radial direction disposed outside, in the radial direction, of the reflecting portion.

17. The air-conditioning apparatus of claim 14, wherein the emitting portion has a rear end in the radial direction disposed outside, in the radial direction, of the reflecting portion.

18. The air-conditioning apparatus of claim 1, wherein the plane perpendicular to the outflow direction, on which ultraviolet ray is reflected, has a thickness corresponding to a flux of ultraviolet ray that is emitted.

\* \* \* \* \*